(12) United States Patent
McGinness et al.

(10) Patent No.: US 12,133,619 B2
(45) Date of Patent: Nov. 5, 2024

(54) VERIFICATION OF CLEANING PROCESS EFFICACY

(71) Applicant: Ecolab USA Inc., St. Paul, MN (US)

(72) Inventors: Rachel Marie McGinness, Rosemount, MN (US); Conor Sylvester Smith, Saint Louis Park, MN (US); Paul R. Kraus, Apple Valley, MN (US); Paul Dominic Christian, Apple Valley, MN (US)

(73) Assignee: Ecolab USA Inc., St. Paul, MN (US)

( * ) Notice: Subject to any disclaimer, the term of this patent is extended or adjusted under 35 U.S.C. 154(b) by 381 days.

(21) Appl. No.: 17/108,894

(22) Filed: Dec. 1, 2020

(65) Prior Publication Data

US 2021/0161355 A1    Jun. 3, 2021

Related U.S. Application Data

(60) Provisional application No. 62/942,801, filed on Dec. 3, 2019.

(51) Int. Cl.
| | | |
|---|---|---|
| *A47L 15/00* | (2006.01) | |
| *G06T 7/00* | (2017.01) | |
| *G06T 7/90* | (2017.01) | |

(52) U.S. Cl.
CPC ....... *A47L 15/0049* (2013.01); *A47L 15/0015* (2013.01); *G06T 7/0008* (2013.01);
(Continued)

(58) Field of Classification Search
None
See application file for complete search history.

(56) References Cited

U.S. PATENT DOCUMENTS

| | | |
|---|---|---|
| D227,117 S | 6/1973 | Breger |
| 4,735,219 A | 4/1988 | Seeland |
| | (Continued) | |

FOREIGN PATENT DOCUMENTS

| | | |
|---|---|---|
| CA | 2541480 A1 | 9/2006 |
| CN | 101961237 A | 2/2011 |
| | (Continued) | |

OTHER PUBLICATIONS

International Search Report and Written Opinion of International Application No. PCT/US2020/062740, dated Mar. 25, 2021, 16 pp.
(Continued)

*Primary Examiner* — Rita P Adhlakha
(74) *Attorney, Agent, or Firm* — Shumaker & Sieffert, P.A.

(57) ABSTRACT

Experimental color data obtained from a plurality of cleaning process verification coupons is used to determine optimized cleaning process parameters in an automated cleaning machine. Color data may also be obtained from cleaning process verification coupon(s) to verify the efficacy of a real-world cleaning processes in an automated cleaning machine and/or to obtain one or more suggested corrective action(s) in the event the cleaning process yields an unsatisfactory cleaning result. Based on the optimized cleaning process parameters, an automated cleaning machine may automatically adjust one or more cleaning process parameters to correct for non-optimized parameters sensed during execution of a cleaning process to help prevent an unsatisfactory cleaning result.

17 Claims, 10 Drawing Sheets

(52) U.S. Cl.
CPC .............. *G06T 7/90* (2017.01); *A47L 2501/26* (2013.01); *G06T 2207/10024* (2013.01); *G06T 2207/30124* (2013.01)

(56) References Cited

U.S. PATENT DOCUMENTS

| | | | |
|---|---|---|---|
| D427,315 S | 6/2000 | Saltzstein et al. | |
| 6,463,940 B1 | 10/2002 | Thomas et al. | |
| 6,615,850 B1 | 9/2003 | Hornung | |
| 7,437,213 B2 | 10/2008 | Batcher | |
| D605,588 S | 12/2009 | Nomi et al. | |
| D677,669 S | 3/2013 | Liu | |
| D699,246 S | 2/2014 | Ringlein | |
| D715,284 S | 10/2014 | Iwamoto | |
| 9,041,985 B2 | 5/2015 | Kasahara et al. | |
| D730,886 S | 6/2015 | Tseng | |
| 9,289,107 B2 | 3/2016 | Ellingson et al. | |
| 9,329,159 B2 | 5/2016 | Walicki | |
| D768,138 S | 10/2016 | Malsan | |
| 9,473,653 B2 | 10/2016 | Hayashi | |
| D788,778 S | 6/2017 | Magi et al. | |
| D795,323 S | 8/2017 | Melamed et al. | |
| D808,947 S | 1/2018 | Taniho et al. | |
| D837,180 S | 1/2019 | Silva | |
| 10,514,339 B2 | 12/2019 | Chen et al. | |
| D872,072 S | 1/2020 | Anderson | |
| 10,529,219 B2 | 1/2020 | Herdt et al. | |
| 10,762,617 B2 | 9/2020 | Sanders et al. | |
| 11,393,083 B2 | 7/2022 | Sanders et al. | |
| 11,803,957 B2 | 10/2023 | Sanders et al. | |
| 2005/0201898 A1 | 9/2005 | Borich et al. | |
| 2006/0222567 A1 | 10/2006 | Kloepfer et al. | |
| 2008/0267445 A1 | 10/2008 | Capewell | |
| 2010/0205819 A1 | 8/2010 | Ashrafzadeh et al. | |
| 2011/0209729 A1 | 9/2011 | Beaudet et al. | |
| 2011/0291830 A1 | 12/2011 | Kaiser | |
| 2011/0320133 A1* | 12/2011 | Mehus ............... | A47L 15/0055 702/23 |
| 2012/0138092 A1 | 6/2012 | Ashrafzadeh et al. | |
| 2014/0041688 A1 | 2/2014 | Maennle et al. | |
| 2014/0218385 A1 | 8/2014 | Carmi | |
| 2015/0233898 A1 | 8/2015 | Chen et al. | |
| 2016/0171690 A1 | 6/2016 | Adiri et al. | |
| 2017/0023542 A1 | 1/2017 | Wang et al. | |
| 2018/0330338 A1 | 11/2018 | Holden et al. | |
| 2019/0244375 A1 | 8/2019 | Choi et al. | |
| 2019/0261828 A1 | 8/2019 | Gaus et al. | |
| 2019/0365197 A1 | 12/2019 | Maddux | |
| 2021/0019874 A1 | 1/2021 | Sanders et al. | |
| 2021/0076898 A1 | 3/2021 | Smith et al. | |
| 2021/0127939 A1 | 5/2021 | Hofmann et al. | |

FOREIGN PATENT DOCUMENTS

| | | |
|---|---|---|
| CN | 107485356 A | 12/2017 |
| CN | 107729816 A | 2/2018 |
| CN | 104668252 B | 1/2019 |
| CN | 10367898 A | 10/2019 |
| CN | 110367898 A | 10/2019 |
| CN | 107421918 B | 12/2019 |
| DE | 102005033345 A1 | 1/2007 |
| DE | 102008042290 A1 | 3/2010 |
| DE | 102010033016 A1 | 2/2012 |
| DE | 102018108775 A1 | 10/2019 |
| EP | 0341766 A2 | 11/1989 |
| EP | 1272093 A2 | 1/2003 |
| EP | 1690924 A1 | 8/2006 |
| EP | 1887443 A1 | 2/2008 |
| EP | 2497404 A1 | 9/2012 |
| EP | 3088593 A1 | 11/2016 |
| JP | 61280838 A | 12/1986 |
| JP | H05115418 A | 5/1993 |
| JP | 2002336335 A | 11/2002 |
| JP | 2009075084 A | 4/2009 |
| KR | 102019102134 A | 8/2019 |
| KR | 102119076 B1 | 6/2020 |
| WO | 9930843 A1 | 6/1999 |
| WO | 0110472 A1 | 2/2001 |
| WO | 0178573 A2 | 10/2001 |
| WO | 0213136 A2 | 2/2002 |
| WO | 2006002123 A1 | 1/2006 |
| WO | 2006097294 A1 | 9/2006 |
| WO | WO-2007081004 A1 * | 7/2007 ............... A61L 2/28 |
| WO | 2010118124 A2 | 10/2010 |
| WO | 2011048575 A2 | 4/2011 |
| WO | 2011089094 A1 | 7/2011 |
| WO | 2014137540 A1 | 9/2014 |
| WO | 2015036311 A1 | 3/2015 |
| WO | 2015080965 A1 | 6/2015 |
| WO | 2015127547 A1 | 9/2015 |
| WO | 2015167574 A1 | 11/2015 |
| WO | 2017056002 A1 | 4/2017 |

OTHER PUBLICATIONS

Office Action from U.S. Appl. No. 17/193,189 dated Nov. 8, 2022, 30 pp.
"Two-Class Logistic Regression," retrieved from https://docs.microsoft.com/en-us/azure/machine-learning/studio-module-reference/two-class-logistic-regression, May 6, 2019, 7 pp.
Narkhede, "Understanding AUC-ROC Curve," towardsdatascience.com, Jun. 26, 2018, 7 pp.
Narkhede, "Understanding Confusion Matrix," towardsdatascience.com, May 9, 2018, 6 pp.
Saslow, "Collinearity-What it Means, Why its Bad, and How Does it Affect Other Models," medium.com, Jul. 11, 2018, 5 pp.
Shung, "Accuracy, Precision, Recall or F1?," towardsdatascience.com, Mar. 15, 2018, 7 pp.
Singh, "Model-Based Feature Importance," towardsdatascience.com, Jan. 3, 2019, 7 pp.
Youtube, "Regularization Part 1: Ridge (L2) Regression," retrieved from https://www.youtube.com/watch?app=desktop&v=Q81RR3yKn30&t=3s, Sep. 24, 2018, 1 pp.
Youtube, "Regularization Part 2: Lasso (L1) Regression," Retrieved from https://www.youtube.com/watch?app=desktop&v=NGf0voTMIcs, Oct. 1, 2018, 1 pp.
International Preliminary Report on Patentability from International Application No. PCT/US2020/062740, dated Jun. 16, 2022, 10 pp.
"CDWA Cleaning Indicator—Cleaning Performance Test," Terragene, retrieved on Feb. 13, 2019, from https://fontlab2000.com/sites/default/files/cdwa-rev.15.pdf, 2 pp.
Powered for iPhone: Wireless Charging Stand for iPhone 8 and Above, Logitech Powered iPhone Wireless Charging Standard, retrieved from https://www.logitech.com/en-us/productlpowered-iphone-wireless-charging?crid=1537 on Mar. 4, 2019, 10 pp.
Kumar et al., "A Detailed Review of Feature Extraction in Image Processing Systems," 2014 Fourth International Conference on Advanced Computing & Communication Technologies, Feb. 8, 2014, 8 pp.
Patel, "Machine Learning Algorithm Overview," medium.com, Jul. 21, 2018, 10 pp.
"NSF/ANSI 3—2017—Commercial Warewashing Equipment," NSF International, ANSI Standard, Apr. 11, 2017, 42 pp.
Brownlee, "A Tour of Machine Learning Algorithms," machinelearningmastery.com, Aug. 14, 2020, 11 pp.
U.S. Appl. No. 17/193,189, filed Mar. 4, 2021, by McGinness et al.
U.S. Appl. No. 17/193,507, filed Mar. 4, 2021, by Han et al.
U.S. Appl. No. 17/193,314, filed Mar. 4, 2021, by Ellingson.
Corrected Notice of Allowance from U.S. Appl. No. 17/193,507, dated Feb. 2, 2023, 5 pp.
Corrected Notice of Allowance from U.S. Appl. No. 17/193,507, dated Mar. 15, 2023, 5 pp.
Notice of Allowance from U.S. Appl. No. 17/193,507 dated Jan. 25, 2023, 10 pp.
Response to Communication Pursuant to Rules 161(1) and 162 EPC dated Jul. 12, 2022, from counterpart European Application No. 20828626.0, filed Jan. 20, 2023, 20 pp.

(56) References Cited

OTHER PUBLICATIONS

Response to Office Action dated Nov. 8, 2022 from U.S. Appl. No. 17/193,189, filed Feb. 8, 2023, 16 pp.
Final Office Action from U.S. Appl. No. 17/193,189 dated May 26, 2023, 32 pp.
Notice of Allowability from U.S. Appl. No. 17/193,507 dated Apr. 28, 2023, 5 pp.
U.S. Appl. No. 18/307,380, filed Apr. 26, 2023, naming inventors Han et al.
Advisory Action from U.S. Appl. No. 17/193,189 dated Aug. 3, 2023, 3 pp.
Response to Office Action mailed May 26, 2023, from U.S. Appl. No. 17/193,189, filed Jul. 26, 2023, 14 pp.
DE102018108775 English translation, accessed on Sep. 2023. (Year: 2019).
Notice of Allowance from U.S. Appl. No. 17/193,189 dated Sep. 27, 2023, 14 pp.
Office Action from U.S. Appl. No. 17/193,314 dated Sep. 13, 2023, 21 pp.
Office Action from counterpart Canadian Application No. 3,161,298 dated Feb. 9, 2024.
Response to Office Action mailed Sep. 13, 2023, from U.S. Appl. No. 17/193,314, filed Dec. 13, 2023, 13 pp.
U.S. Appl. No. 18/398,859, filed Dec. 28, 2023, by McGinness et al.
Final Office Action from U.S. Appl. No. 17/193,314 dated Mar. 27, 2024, 19 pp.
Advisory Action from U.S. Appl. No. 17/193,314 dated Jun. 27, 2024, 3 pp.
First Office Action and Search Report, and translation thereof, from counterpart Chinese Application No. 202080077808.3 dated Jul. 15, 2024, 34 pp.
Response to Final Office Action dated Mar. 27, 2024 from U.S. Appl. No. 17/193,314, filed Jul. 12, 2024, 12 pp.
Response to Final Office Action dated Mar. 27, 2024 from U.S. Appl. No. 17/193,314, filed May 24, 2024, 10 pp.
Response to Office Action dated Feb. 9, 2024, from counterpart Canadian Application No. 3,161,298, filed Jun. 5, 2024, 49 pp.
The Notification of Rejection, and translation thereof, from counterpart Japanese Application No. 2022-533203 dated May 21, 2024, 14 pp.
Notice of Allowance from U.S. Appl. No. 17/193,314, dated Sep. 11, 2024, 10 pp.
Response to Office Action, and translation thereof, dated May 21, 2024, from counterpart Japanese Application No. 2022-533203 filed Aug. 19, 2024, 26 pp.

\* cited by examiner

VERIFICATION OF CLEANING PROCESS EFFICACY

VERIFICATION OF CLEANING PROCESS EFFICACY

This application claims the benefit of U.S. Provisional Application No. 62/942,801, titled, "VERIFICATION OF CLEANING PROCESS EFFICACY", filed Dec. 3, 2019, the entire content of which is incorporated herein by reference.

BACKGROUND

Automated cleaning machines are used in restaurants, healthcare facilities, and other locations to clean, disinfect, and/or sanitize various articles. In a restaurant or food processing facility, automated cleaning machines (e.g., dishmachines) may be used to clean food preparation and eating articles, such as dishware, glassware, pots, pans, utensils, food processing equipment, and other items. In healthcare facilities, for example, automated washer disinfectors may be used to clean and sterilize medical/surgical instrumentation and other medical items. In general, articles to be cleaned are placed on a rack and provided to a wash chamber of the automated cleaning machine. In the chamber, one or more cleaning products and/or rinse agents are applied to the articles during a cleaning process. The cleaning process may include one or more wash phases and one or more rinse phases. At the end of the cleaning process, the rack and the items are removed from the wash chamber. Water pressure, water quality, concentration of the chemical cleaning agents, temperature, cycle duration and other factors may impact the efficacy of a cleaning process.

SUMMARY

In one example, the disclosure is directed to a system that determines an efficacy of a cleaning process based on color data from a verification coupon that was exposed to the cleaning process, wherein the color data includes at least one of a red-green ratio, a blue-green ratio, a red-blue ratio, or a percent color value.

In another example, the disclosure is directed to a method for determining an efficacy of a cleaning process based on color data from a verification coupon that was exposed to the cleaning process, wherein the color data includes at least one of a red-green ratio, a blue-green ratio, a red-blue ratio, or a percent color value.

In another example, the disclosure is directed to a method of training a computer system to determine an efficacy of a cleaning process based on color data from a plurality of verification coupons that were exposed to a plurality of experimental cleaning processes, wherein the color data includes at least one of a red-green ratio, a blue-green ratio, a red-blue ratio, or a percent color value.

In another example, the disclosure is directed to an automated cleaning machine that receives sensed values for one or more cleaning process parameters during execution of a cleaning process, determines that whether one or more of the sensed values do not satisfy their respective optimized cleaning process parameter values, and adjusts a cleaning machine setting associated with a different one of the cleaning process parameters to ensure a satisfactory cleaning result during execution of a subsequent cleaning process.

In another example, the disclosure is directed to an automated cleaning machine comprising: at least one processor; at least one sensor that senses information concerning one or more cleaning process parameters during execution of a cleaning process in a wash chamber of the cleaning machine; and a storage device comprising instructions executable by the at least one processor to: receive the sensed information concerning the one or more cleaning process parameters during execution of the cleaning process; determine, based on the sensed information, that one or more of the cleaning process parameters sensed during execution of the cleaning process does not satisfy a corresponding optimized cleaning process parameter value; and adjust a cleaning machine setting associated with a different one of the cleaning process parameters.

The one or more cleaning process parameters sensed during execution of the cleaning process may include a wash cycle duration, a rinse cycle duration, a detergent concentration, a wash water temperature and a rinse water temperature. The one or more cleaning process parameters sensed during execution of the cleaning process may include a rinse aid concentration or an incoming water temperature.

The one or more cleaning process parameters may include a wash water temperature, and the adjusted cleaning machine setting may include a wash cycle duration. The one or more cleaning process parameters may include a detergent concentration, and the adjusted cleaning machine setting may include a wash cycle duration. The one or more cleaning process parameters may include a wash water temperature, and the adjusted cleaning machine setting may include a detergent concentration.

The storage device may further comprise instructions executable by the at least one processor to initiate a sump water dump/fill cycle. The storage device may further comprise instructions executable by the at least one processor to initiate a de-liming cycle.

The storage device may further comprise instructions executable by the at least one processor to: generate a notification indicating that one or more of the cleaning process parameter values sensed during execution of the cleaning process did not satisfy the corresponding optimized cleaning process parameter value. The storage device may further comprise instructions executable by the at least one processor to: generate a notification including one or more corrective actions that may be taken to address a failure of the one or more cleaning process parameters to satisfy the corresponding optimized cleaning process parameter value. The storage device may further comprise instructions executable by the at least one processor to: apply the adjusted cleaning process parameters during execution of the cleaning process. The storage device may further comprise instructions executable by the at least one process to: apply the adjusted cleaning process parameters during execution of a subsequent cleaning process.

In another example, the disclosure is directed to a non-volatile computer-readable storage medium storing instructions that, when executed, cause one or more processors to: receive sensed information concerning one or more cleaning process parameters during execution of a cleaning process within a wash chamber of a cleaning machine; determine, based on the sensed information, that one or more of the cleaning process parameters sensed during execution of the cleaning process does not satisfy a corresponding optimized cleaning process parameter value; and adjust a cleaning machine setting associated with a different one of the cleaning process parameters.

In another example, the disclosure is directed to a system comprising: an automated cleaning machine comprising: at least one processor; at least one sensor that senses information concerning one or more cleaning process parameters during execution of a cleaning process in a wash chamber of the cleaning machine; and a storage device comprising instructions executable by the at least one processor to: receive the sensed information concerning the one or more cleaning process parameters during execution of the cleaning process; determine, based on the sensed information, that one or more of the cleaning process parameters sensed during execution of the cleaning process does not satisfy a corresponding optimized cleaning process parameter value; and adjust a cleaning machine setting associated with a different one of the cleaning process parameters.

The system may further include a computing device comprising: at least one processor; a storage device comprising instructions executable by the at least one processor of the computing device to: obtain color data from a verification coupon that was exposed to the cleaning process, wherein the color data includes at least one of a red-green ratio, a blue-green ratio, a red-blue ratio, or a percent color value; and determine an efficacy of the cleaning process based on the color data. The characteristic soil may include a food-based soil or an organic soil.

The details of one or more examples are set forth in the accompanying drawings and the description below. Other features will be apparent from the description and drawings, and from the claims.

DETAILED DESCRIPTION

Figure 1:
FIG. 1 shows an example cleaning process verification coupon having a test soil within a verification area of a substrate.

In accordance with one aspect of the present disclosure, experimental color data obtained from a plurality of cleaning process verification coupons is used to determine optimized cleaning process parameters in an automated cleaning machine. Color data may also be obtained from cleaning process verification coupon(s) to verify the efficacy of a real-world cleaning process(es) in an automated cleaning machine and/or to obtain one or more suggested corrective action(s) in the event the cleaning process yields an unsatisfactory cleaning result. In accordance with another aspect of the present disclosure, based on the optimized cleaning process parameters, an automated cleaning machine may automatically adjust one or more cleaning process parameters to correct for non-optimized parameters sensed during execution of a cleaning process to help prevent an unsatisfactory cleaning result.

During an experimental optimization phase, and/or during a real-world verification phase, one or more verification coupons are placed in the washing chamber of an automated cleaning machine. Each verification coupon includes a substrate having at least one test indicator within a verification area of the substrate. The test indicator undergoes a change, such as complete removal, partial removal or a color change, when exposed to a cleaning process within the automated cleaning machine. The amount or degree of the change is a function of the efficacy of the cleaning process, and can be used to quantify the efficacy of the cleaning process and/or to identify failures in one or more cleaning process parameters that may have resulted in an unsatisfactory cleaning result. This means that the process is able to deliver a quantitative value which is proportional to or indicative of the performance of overall cleaning process.

To quantify the amount or degree of change of a test indicator as a result of a cleaning process, or, to quantify the amount of a test indictor remaining on the coupon after completion of a cleaning process, color data is obtained from a reading of the verification area of the verification coupon. The color data may include an intensity of one or more colors, such as a red wavelength range, a blue wavelength range, a green wavelength range, or a grayscale wavelength range. The color data may also include one or more of wavelengths in an infrared (IR) or ultraviolet (UV) color range. The color data may also include, for example, one or more RGB ratios of the verification area. The RGB ratios may include, for example, a red/green ratio (R/G), a red/blue ratio (RB), a blue/green (B/G) ratio, and/or a C/G color ratio. In addition, or alternatively, in some examples, the color data may include one or more percent color values. The percent color values may include, for example, a percent red (% R), a percent blue (% B), and/or a percent green (% G). In some examples, the color data may further include a FIJI gray value.

If a defined color change or defined color measurement is detected as a result of the analysis, the cleaning process may be determined to be satisfactory. If the defined color change or defined color measurement was not detected as a result of the analysis, the cleaning process performance may be deemed unsatisfactory. The results obtained from analysis of the verification coupons from a plurality of cleaning processes during the optimization phase may be used to determine optimized cleaning process parameters that will lead to a satisfactory cleaning result for the cleaning machine.

In addition, the results obtained from analysis of the verification coupons from a plurality of cleaning processes during the optimization phase may be used to determine adjusted optimized cleaning process parameters to help ensure a satisfactory cleaning result in real-world situations where one or more cleaning process parameters measured during a cleaning process do not meet the optimized parameter values (or range of values). In other words, the analysis during the optimization phase may determine how one or more optimized cleaning process parameters may be automatically adjusted to compensate for the failure of other cleaning process parameters to satisfy their respective optimized parameter values during a real-world cleaning process. In this way, a cleaning machine may automatically self-adjust in the field if it detects that one or more cleaning process parameters are "out of spec" during execution of a real-world cleaning process to ensure that a satisfactory cleaning result is achieved even when certain optimized cleaning process parameters are not or cannot be met. The cleaning machine may automatically adjust one or more cleaning process parameters and apply those adjusted cleaning process parameters during execution of the cleaning process, or it may automatically adjust one or more parameters after completion of the cleaning process and may apply the adjusted cleaning process parameters during execution of a subsequent cleaning process.

For verification of a real-world cleaning process, one or more verification coupons subjected to the cleaning process may be scanned to obtain color data associated with the cleaning process. The system may analyze color data obtained from the scan to determine whether the cleaning process was satisfactory. The system may further generate an indication for display on a user computing device, or may generate some other type of electronic communication, indicating the results of the analysis (e.g., whether the result of the cleaning process verification is "pass" or "fail").

In the event that the cleaning process performance is unsatisfactory, further analysis of the color data may identify one or more cleaning process parameters whose failure may have led to the unsatisfactory result. Such potential failures in the cleaning process may be investigated and/or addressed so that future cleaning processes may be satisfactorily verified. In some examples, the system may generate an indication for display on a user computing device, or may generate some other type of electronic communication, indicative of the potential failures in the one or more cleaning process parameters of the cleaning process. The communication may also indicate how those potential failures may be investigated and/or suggest corrective action which may be taken to address the potential failures.

In some examples, the cleaning process verification procedure may be performed on a periodic basis in accordance with a cleaning process verification plan established by a business entity. Verification of the cleaning process can help to ensure proper cleaning, disinfection and/or sterilization of articles to be cleaned.

In some examples, the test indicator(s) may include one or more soils that are commonly experienced by the automated cleaning machine and that are expected to be satisfactorily removed by the cleaning process. The test indicator(s) may be designed to represent the soil(s) typically encountered by the application. In a healthcare application, for example, the test indicator(s) may include medical soil(s) (those typically found or representative of those encountered in a medical environment), which may further include organic soils such as protein, lipids, carbohydrates, bone chips, etc., and/or inorganic soils such as saline, bone cement, calcium and other minerals, dyes, inks, etc. In a restaurant or food processing application, the test indicator(s) may include any type of food-based soil(s) such as fats and oils, proteins, carbohydrates, dyes, minerals, starches, coffee and tea stains, etc., and/or other soils commonly encountered in a food establishment such as dyes, inks, lipstick, dimethicone or other cosmetic soils. In some examples, the test indicators may be customized so as to most closely represent the type of soils encountered during the cleaning processes of a particular application. Other possible test indicators for these and other applications will be apparent to those of ordinary skill in the art, and the disclosure is not limited in this respect.

The color data obtained from a reading of the verification area after completion of the cleaning process may be compared to one or more thresholds indicative of various levels of cleaning performance. For example, one or more RGB ratios, percent color values, FIJI gray values, or other color data may be compared to corresponding threshold values to quantify the level of cleaning performance. Each RGB ratio, percent color value, FIJI gray value (or other color data) may have one or more corresponding threshold values, where each corresponding threshold value is indicative of a level of cleaning performance. The levels of cleaning performance may include, for example, clean (or "pass") and soiled (or "fail"). The levels of cleaning performance may further include various levels of "soiled." In some examples, each "soiled" level includes identification of potential failures of one or more cleaning process parameters that may have resulted in the unsatisfactory result of the overall cleaning process. For example, certain levels of "soiled" may indicate potential failures of certain cleaning process parameters, while other levels of "soiled" may indicate potential failures of different cleaning process parameters (e.g., temperature vs. amount of detergent), or different types of failures with the same cleaning process parameter (e.g., temperature too high vs. temperature too low).

The cleaning process parameters may include, for example, wash and rinse times and sequences, wash and rinse water temperatures, wash and rinse water conductivities, wash and rinse water pH, detergent concentration, rinse agent concentration, humidity, water hardness, turbidity, rack temperatures, mechanical action within the cleaning machine, and any other cleaning process parameter that may influence the efficacy of the cleaning process.

The cleaning process verification coupon may be placed at any appropriate location or orientation within the washing environment of the cleaning machine so as to experience a representative cleaning process within the machine. For example, the verification coupon may be positioned where it will be exposed to the same cleaning process experience as articles to be cleaned would experience. If the verification coupon is run through the cleaning process during the same cleaning cycle as articles to be cleaned, the verification coupon may be positioned where it will not block or inhibit flow of cleaning solution, water, steam, air, heat, or other cleaning component circulated throughout the wash chamber, nor inhibit operation of the cleaning machine. In addition, multiple verification coupons may be placed at different locations within the cleaning machine during the same cleaning process to monitor cleaning process conditions at those different locations within the machine.

During an optimization or verification procedure, one or more verification coupons, including the test indicator deposited or printed within the verification area, is placed inside the wash chamber of a cleaning machine, such as on or in a rack, on or in an article to be cleaned, mounted to a sidewall within the cleaning machine, etc., and subjected to the cleaning process within the cleaning machine. The verification coupon(s) is cleaned by the combination of the chemistry (active cleaning ingredients) in the cleaning solution and any mechanical action (such as impingement onto or flow of the cleaning solution over the verification coupon) taking place within the cleaning machine. Other factors that may influence the efficacy of the cleaning process include, but are not limited to, the duration of the cleaning process, including the relative duration of each step or cycle within the overall cleaning process (e.g., wash time and rinse time), water temperature throughout the cleaning process (e.g., sump water temperature, wash water temperature and/or rinse water temperature), water hardness and/or turbidity; detergent concentration, rinse agent concentration, conductivity of the wash and/or rinse water, adherence to defined procedures concerning operation of the cleaning machine, proper mechanical operation of the cleaning machine, etc.

After completion of the cleaning process, the test indicator should experience a defined change, or a defined color measurement, after completion of the cleaning process. The defined change or color measurement may include a defined color change or color measurement as determined by analysis of a color reading of the verification area, and which is indicative of satisfactory removal of the test indicator by the cleaning process or of a satisfactory amount of test indicator remaining after completion of the cleaning process.

Information concerning the amount of soil remaining on the coupon may be captured after completion of the cleaning process. This information may be obtained, for example, from a color scan measurement of the coupon (such as by using a colorimeter), a digital image of the coupon, or other means of obtaining digital information concerning the amount of soil remaining on the coupon. The information may be obtained inside the wash chamber or outside of the wash chamber of the cleaning machine. The information may be captured automatically by a color sensor or digital camera, or the capture of the information may be initiated manually by a user. One or more intermediate or additional steps may also be included, such as applying a dye to the verification area of the verification coupon, and/or obtaining a color scan measurement or digital image of the dyed verification area.

Figure 2:
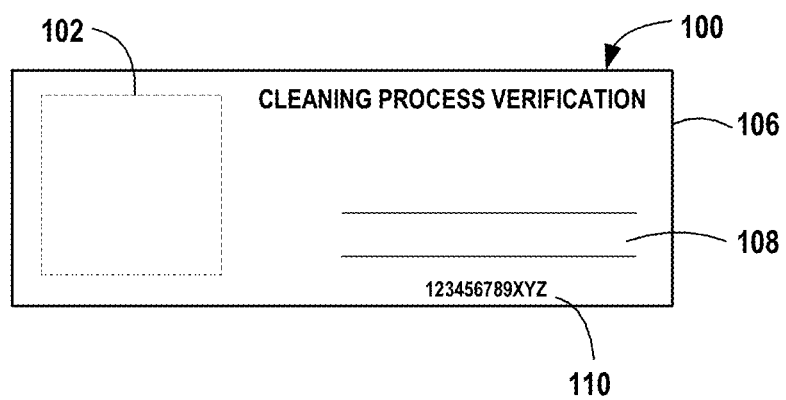
FIG. 2 shows the example verification coupon of FIG. 1 with the test soil completely removed.

FIG. 1 shows an example cleaning process verification coupon 100. Verification coupon includes a substrate 106 having a test indicator 104 within a verification area 102. FIG. 2 shows the example cleaning process verification coupon 100 of FIG. 1 in which test indicator 102 has been completely removed by a cleaning process.

Substrate 106 may include any type of temperature stable material such as plastics, papers, metals, or ceramics. Examples of suitable substrate materials include, but are not limited to, polyethylene, polypropylene, polyester, polyvinyl chloride (vinyl), high density polyethylene (HDPE), synthetic forms of paper, plastics, ceramics, stainless steel and other metals. Test indicator 104 may be printed, ink-jet printed, screen printed, spray coated, dip coated, or otherwise deposited on substrate 106. In this example, test indicator 104 is octagonal in shape; however, it shall be understood that the test indicator 104 may take any desired regular or irregular shape, and that the disclosure is not limited in this respect.

Verification coupon 100 may also include one or more other areas, such as a writable area 108, which allows a user to add identification information or other notes to verification coupon 100. The identification information may include, for example, the date and time of the cleaning cycle, identification of the cleaning machine, identification of the person running the cleaning cycle and/or the verification procedure, a "clean" or "soiled" indication, and/or other information relevant to the cleaning process verification procedure. The verification coupon 100 may further include a printed identifier 110 uniquely identifying the coupon. In the example of FIG. 1, identifier 110 is a serial number visually readable by a human being, and/or electronically readable by a computing device. In other examples, identifier 110 may also include one or more of a bar code, a QR code, or other type of electronically readable identifier or code.

Each verification coupon 100 and test indicator 104 is designed to represent soils experienced in a particular application and to be responsive to cleaning process(es) appropriate for those applications. For example, in a restaurant or other food establishment, the automated cleaning machines may include automated dish machines and the cleaning processes may be expected to remove food and/or other soils typically encountered in such applications. The test indicator(s) designed for such applications may therefore include food-based soil(s) such as fats and oils, proteins, carbohydrates, food dyes, minerals, starches, coffee and tea stains, etc., or other soils commonly encountered in a food establishment such as dyes, inks, lipstick or other cosmetic soils. In a healthcare application, the test indicator(s) may include those typically found or representative of those encountered in a medical environment), which may further include organic soils such as protein, lipids, carbohydrates, bone chips, etc., and/or inorganic soils such as saline, simethicone, bone cement, calcium and other minerals, dyes, inks, etc. In other applications, the test indicator(s) may include those soils or stains typically found or representative of those encountered in such applications, and the disclosure is not limited in this respect. It shall be understood, therefore, that verification coupon 100 is but one example of an verification coupon that may be used according to the techniques of the present disclosure, and that the disclosure is not limited in this respect.

Figure 3:
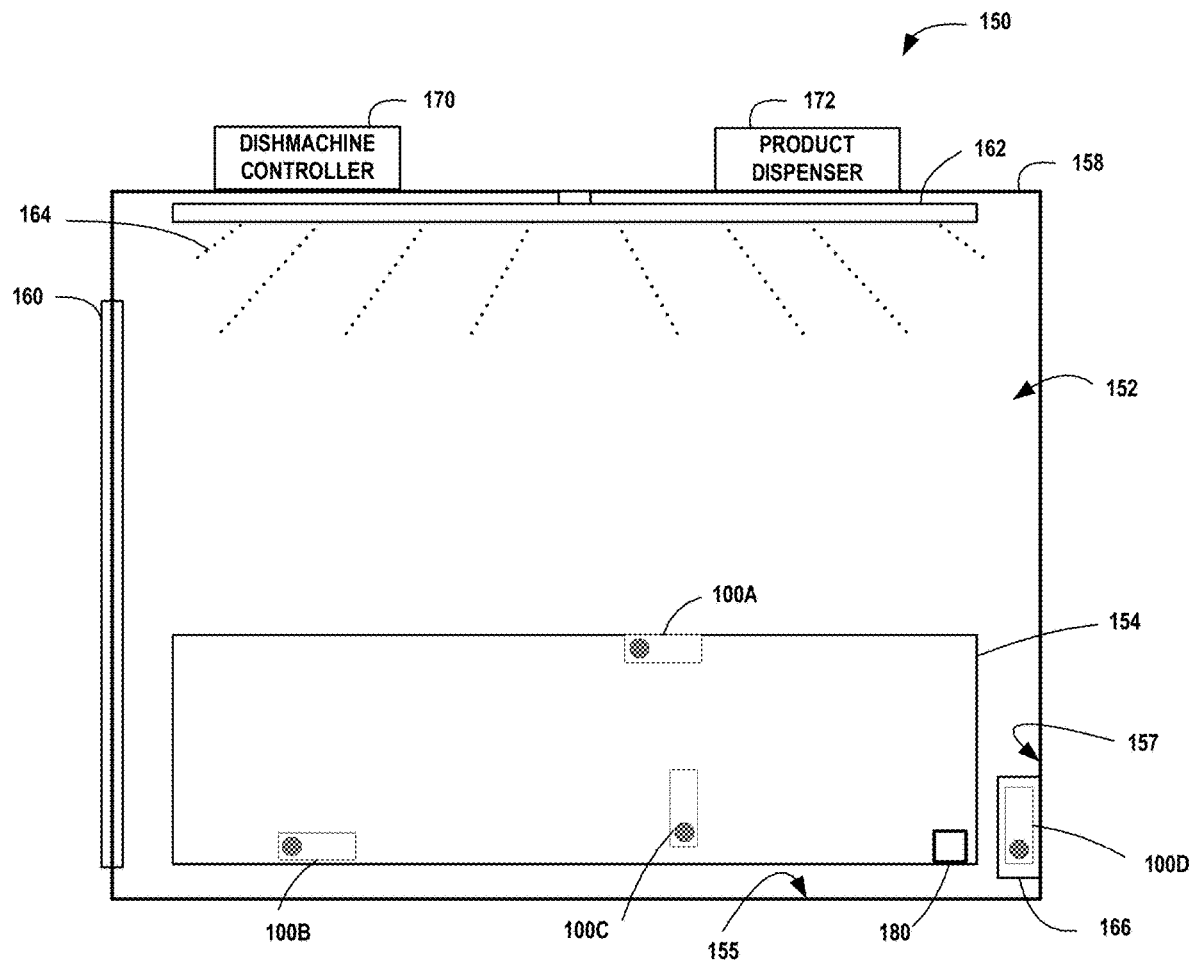
FIG. 3 shows an example automated cleaning machine in which one or more verification coupons are used to verify a cleaning process in accordance with the present disclosure.

FIG. 3 shows an example automated cleaning machine 150 in which one or more cleaning process verification coupons 100A-100D (collectively, "verification coupons 100") may be used to verify a cleaning process in accordance with the present disclosure. In this example, cleaning machine 150 is a dishmachine for cleaning eating and/or food preparation articles including one or more of pots and pans, dishware, glassware, eating and cooking utensils, etc. It shall be understood, however, that cleaning machine 150 may include any other type of cleaning machine such as clothes or textile washing machines, medical instrument reprocessors, automated washer disinfectors, autoclaves, sterilizers, or any other type of cleaning machine, and that the disclosure is not limited in this respect.

Cleaning machine 150 includes an enclosure 158 defining one or more wash chamber(s) 152 and having one or more door(s) 160 that permit entry and/or exit into wash chamber 152. One or more removable rack(s) 154 are sized to fit inside wash chamber 152. Each rack 154 may be configured to receive articles to be cleaned directly thereon, or they may be configured to receive one or more trays or holders into which articles to be cleaned are held during the cleaning process. The racks 154 may be general or special-purpose racks, and may be configured to hold large and/or small items, food processing/preparation equipment such as pots, pans, cooking utensils, etc., and/or glassware, dishes and other eating utensils, etc. In a hospital or healthcare application, the racks may be configured to hold instrument trays, hardgoods, medical devices, tubing, masks, basins, bowls, bed pans, or other medical items. It shall be understood that the configuration of racks 154, and the description of the items that may be placed on or in racks 154, as shown and described with respect to FIG. 1 and throughout this specification, are for example purposes only, and that the disclosure is not limited in this respect.

A typical cleaning machine such as cleaning machine 150 operates by spraying one or more cleaning solution(s) 164 (a mixture of water and one or more chemical cleaning products) into wash chamber 152 and thus onto the articles to be cleaned. The cleaning solution(s) are pumped to one or more spray arms 162, which spray the cleaning solution(s) 164 into wash chamber 152 at the appropriate times. Cleaning machine 150 is provided with a source of fresh water and, depending upon the application, may also include one or more sumps to hold used wash and/or rinse solution to be reused in the next cleaning cycle. Cleaning machine 150 may also include or be provided with a chemical product dispenser 172 that automatically dispenses the appropriate chemical cleaning product(s) at the appropriate time(s) during the cleaning process. The chemical products are mixed with the diluent, and the resulting cleaning solution(s) 164 are pumped into the wash chamber 152 via spray arms 162 at the appropriate time(s). Depending upon the machine, the articles to be cleaned, the amount of soil on the articles to be cleaned, and other factors, one or more wash cycles may be interspersed with one or more rinse and/or sanitization cycles to form one complete cleaning process of cleaning machine 150.

Automated cleaning machine 150 further includes a dishmachine controller 170. Controller 170 may further be configured to communicate with an automated chemical product dispenser 172. Controller 170 includes one or more processor(s) that monitor and control various cleaning process parameters of the cleaning machine 150 and/or product dispenser 172 such as cycle time(s) and length(s), cleaning solution concentrations, wash water conductivity, timing for and amounts of chemical product(s) dispensed, wash water temperature(s), rinse water temperature(s), heated air temperature(s), wash chamber temperature(s), humidity, timing of application of water and chemical products into the wash chamber, etc.

As shown in FIG. 3, one or more cleaning process verification coupon(s), such as verification coupon(s) 100A-100D, may be placed in various locations within the wash chamber 152 or on or in rack(s) 154 during a cleaning process. In this example, verification coupons 100A-100C are located in or on rack 154. Coupon 100D is located in a mounting bracket or holder 166 affixed to a sidewall 157 of wash chamber 152. Placing multiple verification coupons, such as coupons 100A-100D, in different areas of the wash chamber 152 as shown in FIG. 3 may help to verify the completeness and efficacy of the cleaning process throughout the entire wash chamber 152. In other examples, a single one of verification coupons 100 may be used for each cleaning cycle. The number of verification coupons used per cleaning cycle may depend upon the type of articles to be cleaned, the type of cleaning machine, the type(s) of soil to be removed, and/or the cleaning process and verification procedures defined by the enterprise or business entity, among other things. It shall be understood, therefore, one or more verification coupons may be used with each cleaning cycle, and that the number of verification coupons used per cleaning cycle is not limited in this respect.

A verification coupon mounting bracket, holder, clip, or other fastener, such as coupon holder 166, may be configured to support or hold a verification coupon during a cleaning process. In some examples, the holder, clip or other fastener may be manually attached to or placed in or on a rack 154 or one or more walls of the wash chamber 152 prior to the start of a cleaning process. In other examples, the holder, clip or fastener may be molded directly into one or more walls of the wash chamber 152, or molded directly onto a rack 154. In that example, the verification coupon would be placed into the molded holder prior to the start of the cleaning process. In other examples, the fastener or holder may include a screw, a push-in plastic rod, a circular protrusion that would fit into a hole in a rack or tray, a rib that would snap in to a matching slot feature on a rack or tray, or by using a clip modified either during molding of the rack or the rack may need to be retrofitted. It shall be understood that the coupon holder may be any of suitable type, and that the disclosure is not limited in this respect.

In some examples, the coupon holder is designed to simulate a realistic challenge to the cleaning process of the types of articles to be cleaned. For example, items such as certain types of cooking equipment, utensils, medical devices or surgical instrumentation may include harder to reach areas that are more difficult to thoroughly clean during a cleaning process. To that end, the coupon holder may include walls having one or more screens, apertures, or slots that at least partially obscure the verification area of a verification coupon to provide a more realistic challenge to the cleaning process. It shall be understood that a coupon holder is optional and that the disclosure is not limited in this respect.

One or more verification coupon(s) 100 may be placed at any location within the wash chamber 152, and may be located in position(s) where they do not interfere with the spray of the cleaning solution(s) and/or mechanical operation of cleaning machine 150. Verification coupons 100 may further be of an appropriate size so as not block spray of the cleaning solution during the cleaning process or interfere with mechanical operation of cleaning machine 150.

In some examples, verification coupons 100 are rectangular in shape and have overall dimensions (length and width) of sufficient size to accommodate suitably sized test indicator(s). It shall be understood that verification coupon(s) 100 may be any suitable size or shape, and further that the test indicator may also vary in shape, depending at least in part on the cleaning application, the type of soil to be removed, and/or the cleaning machine. For example, although the test indicators in FIGS. 1-3 are shown as octagonal in shape, other regular or irregular shapes may also be used, and the disclosure is not limited in this respect. For example, the test indicator may be divided into one or more areas, wherein each area includes the same test indicator or different test indicators. The test indicator(s) may further take the form of a circle, oval, square, triangle, rectangle, pentagon, hexagon, parallelogram, star-shape, splatter-shape, a line or sequence or pattern of lines, regular or irregular polygon, or any other appropriate or desired regular or irregular shape.

Once each the cleaning process is complete, the verification coupon(s) 100 associated with the cleaning process are removed from the cleaning machine 150. A color sensor (see FIGS. 4A-4B), obtains color reading(s) associated with the verification area (e.g., verification area 102) of the coupon 100. The color sensor may include, for example, a colorimeter or other device for obtaining color data from a sample surface. The color reading(s) are transmitted to and received by a computing device (see FIG. 4A), which may analyze the color reading(s) to generate additional color data. The color data may include, for example, one or more RGB ratios. The RGB ratios may include, for example, a red/green ratio (R/G), a red/blue ratio (RB), and/or a blue/green (B/G) ratio. In addition, or alternatively, in some examples, the color data may include one or more percent color values. The percent color values may include, for example, a percent red (% R), a percent blue (% B), and/or a percent green (% G). In some examples, the color data may further include a FIJI gray value. Other color data may also be generated, and the disclosure is not limited in this respect.

In some examples, the test indicator may be stained or dyed to bring about a color change if certain soils remain, such as proteins (Coomassie blue or silver staining methods), carbohydrates, fats, blood, etc. Staining or dying of the test indicator may help to make certain changes in the test indicator more easily detectable under certain conditions.

Color data obtained from multiple experimental cleaning processes during an optimization phase may be used to determine one or more optimized cleaning process parameters for the cleaning machine. In addition, relationships between the cleaning process parameters may be determined such that adjustments to one or more cleaning process parameters may be identified that correct for any non-optimized cleaning process parameters. In this way, a cleaning machine may be programmed to automatically adjust one or more cleaning process parameters to compensate for any non-optimized cleaning process parameters sensed during a real-world cleaning process.

For verification of real-world cleaning processes, the computing device analyzes the color data associated with the verification area. If a defined color change is detected as a result of the analysis, the cleaning process is determined to be satisfactory. If the defined color change is not detected, the cleaning process performance is determined to be unsatisfactory. In the event that the cleaning process performance is determined to be unsatisfactory, further analysis of the color data and/or other data regarding the cleaning process may identify potential failures of one or more cleaning process parameters which may have resulted in the unsatisfactory cleaning results, and may suggest corrective action(s) that may be taken to address the potential failures.

In some examples, the computing device may generate a notification for display that the cleaning process was verified and/or that the cleaning process "passed" the verification procedure. If the cleaning process is determined to be unsatisfactory, the computing device may generate a notification for display that the cleaning cycle was not verified and/or that the cleaning cycle "failed" the verification procedure. In some examples, a fail notification may be generated and displayed that includes possible reasons why the cleaning process was unsatisfactory. The notification may also include suggested corrective action(s) that may be taken by a user to address the potential failures of the identified cleaning process parameters. In some examples, the identified cleaning process parameters may be automatically adjusted to correct for the identified failures.

In some examples, dishmachine 150 uses dish racks with electronically readable identifiers to uniquely identify each rack and to identify the types of article(s) in the rack. In the example of FIG. 3, rack 154 includes an RFID tag 180. The rack identification data stored in RFID tag 180 includes a rack type and a unique rack identifier. The rack type corresponds to the type of articles washed on or in the rack. For example, the rack type may be identified as a pot/pan rack, a glassware rack, a dishware rack, a utensil rack, etc. The rack identifier is uniquely associated with an individual rack. The rack identifier enables individual tracking of each cleaning cycle with a uniquely identified rack and associated rack type, along with a date and time stamp. Example rack identification systems are described in U.S. Pat. Nos. 7,437,213 and 6,463,940, which are incorporated by reference herein in their entirety.

Dishmachine controller 170 includes a tag reader configured to read the RFID tag 180 and obtain the rack identification data. Dishmachine controller 170 (or other computing device) may associate the unique rack identifier with the current cleaning process. This also results in identifying the type of articles that were cleaned during the current cleaning cycle, and linking the individual rack and article type with any other data associated with the current cleaning cycle (e.g., cycle type, water volumes and temperatures, amounts/volumes/weights of chemical product dispensed, cycle times, etc.).

Dishmachine controller 170 further determines the rack type, and thus identifies the type of articles being washed during the current cleaning process. The dishmachine controller 170 may adjust the cleaning process to best address the type(s) of articles being cleaned and the type(s) of soils typically encountered when cleaning those articles. For example, as discussed above, the different types of articles that are cleaned in a dishmachine may experience different types of soils. For example, pots and pans may be soiled with large amounts of starch, sugar, protein, and fatty soils. In contrast, glasses are not typically heavily soiled but have hard to remove soils like lipstick, coffee and tea stains. Once dishmachine controller 170 identifies the type of article in the rack, it can modify the dishmachine cycle in a manner that selects optimal wash/rinse cycles, times, temperatures, and chemical compositions needed to clean the articles while minimizing use of water, energy, or chemical cleaning product. For example, running a wash cycle with chemical compositions that are effective at cleaning pots and pans would likely be too much chemistry for a rack of glasses. Rack identification allows dishmachine controller 170 to use the correct type and concentration of chemistry for the article to be cleaned. And by not overusing chemistry, the dishmachine can use less chemistry overall while still achieving the expected cleaning performance results.

These RFID tags, such as tag 154, may be integrated into the dishmachine rack in many ways. They may be physically attached to the rack by use of a fastener, may be molded directly into the rack, or may be attached to the rack with a molded or machined clip or bracket. They may be located at any location on the rack, but preferably will be located along the outside edge of the rack, so they do not interfere with the spray of water that cleans the dishes. The mounting feature may allow the RFID tag to be attached to both new and pre-existing racks. One method of doing this is with an injection molded bracket that is designed to hold the RFID tag in a specific position on the rack, and can be inserted into many types of racks. In some examples, the tag is placed in a consistent location on each rack, which can be read through an antenna located mounted in, on or near floor 155 or sidewall 157 of the dishmachine. In other examples, the tag reader may be located outside of the dishmachine or on an outside wall of the dishmachine.

Identification of individual racks and rack types, and the cleaning process data that may also be obtained by the dishmachine, may further be analyzed to identify the number and type of wash processes over specified time periods, view historical data on problems encountered during the wash process, view data regarding the general operation of the machine (e.g., how many cycles per day/week/month, how often it is drained, etc.), and the type of ware washed during particular times and days of the week, in addition to cycle times, temperatures, dispensed chemical amounts, and can help create reports to improve management of a dish washing facility.

Identification of rack types may also determine the way in which the color data associated with the verification coupon is analyzed by the computing device. For example, depending upon the type of article being cleaned, different types of verification coupons (and therefore different test indicators) may be used, and each different type of verification coupon may be associated with a different corresponding analysis of the color data. For example, certain test indicators may be analyzed using multiple RGB ratios and/or color values or percentages (for example, two or more of RG, RB, BG, or CG color ratios, and/or the FIJI gray value). In other examples, certain test indicators may require only a single one of the RGB ratios (for example, one of RG, RB, BG, or CG color ratios, and/or the FIJI gray value) for statistically significant results to be obtained. The type of color data and the threshold(s) associated with that color data may depend upon, for example, the color of the test indicator, the formulation of the test indicator, and the types of changes (in color and/or amount) experienced by the test indicator throughout the cleaning process for satisfactory cleaning processes, unsatisfactory cleaning processes, or both.

Figure 4B:
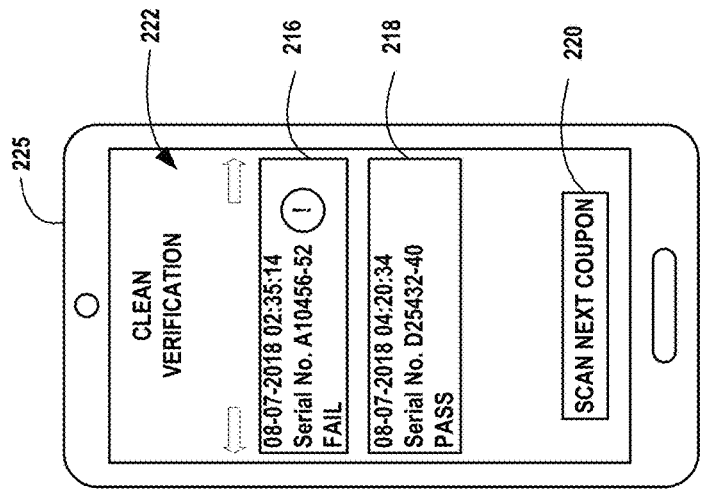
FIG. 4B is a front view of a computing system on which example cleaning process verification notifications are displayed.
Figure 4A:
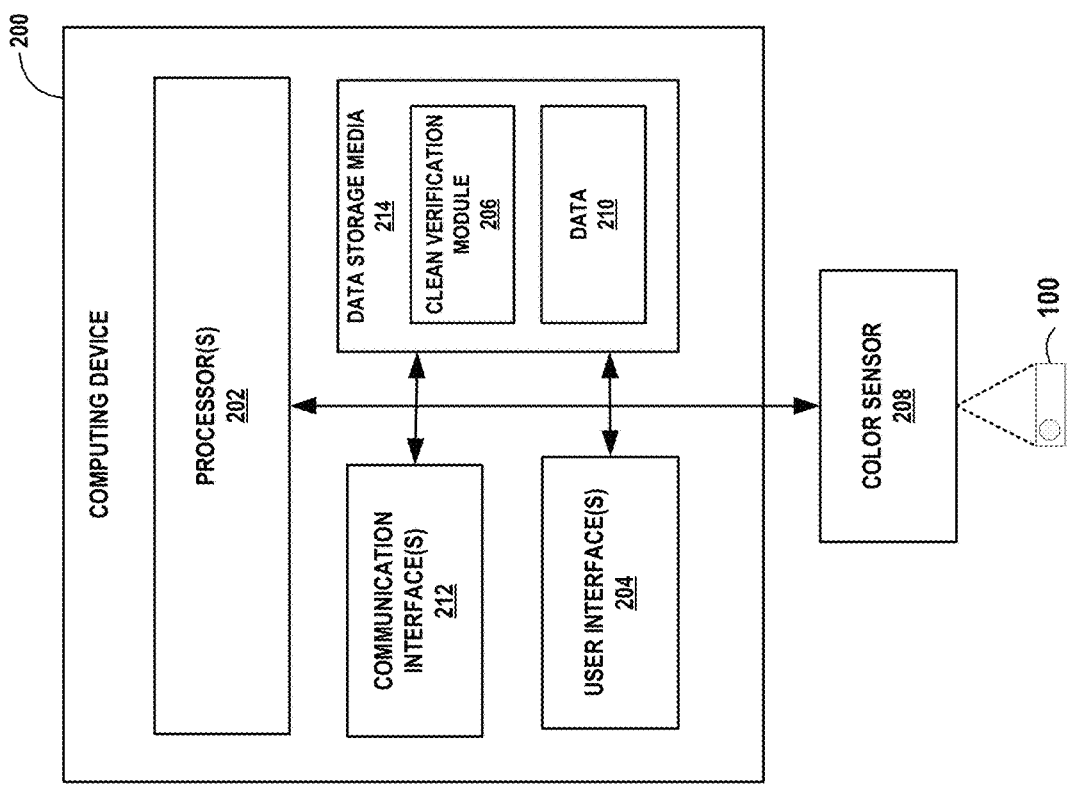
FIG. 4A is a block diagram illustrating an example computing system used to verify an efficacy of a cleaning process in accordance with the present disclosure.

FIG. 4A is a block diagram of an example computing device 200 that may be used to obtain color data associated with a verification coupon and/or to verify a cleaning process based on analysis of color data associated with a verification coupon in accordance with the present disclosure. Computing device 200 may include, for example, a mobile computing device, a smart phone, a tablet computer, a laptop computer, a desktop computer, a server computer, a personal digital assistant (PDA), a portable gaming device, a portable media player, an e-book reader, a wearable computing device, a smartwatch, a television platform, a remote or cloud-based computing device, or any other type of computing device.

Computing device 200 includes one or more processors 202, one or more user interface components 204, one or more communication interfaces 212, a color sensor 208, and data storage media 214. User interface components 204 may include one or more of audio interface(s), visual interface(s), and touch-based interface components, including, for example, a touch screen display, speakers, buttons, keypad, stylus, mouse, or other mechanism that allows a user to interact with a computing device. Communication interfaces 212 allow computing device 200 to communicate with other remote or local computing devices via wired and/or wireless connections. The wired and/or wireless communication may include communication over one or more networks, such as any type of Local or Wide Area Networks, including Wi-Fi networks, Bluetooth communication, Near Field communication, and/or the internet. For example, computing device 200 may communicate with one or more remote computing devices. Data storage media 214 includes a clean verification module 206 and data storage 210. Clean verification module 206 includes computer readable instructions that, when executed by the one or more processors 202, cause the one or more processors 202 to analyze color data associated with a verification coupon and determine the efficacy of the associated cleaning process based on the analysis.

Color sensor 208 may include a color sensor capable of obtaining color readings from a surface. For example, color sensor 208 may include a source that directs white light at a surface (such as the verification area of a verification coupon) and one or more detectors, such as one or more photodiode(s), that sense the color(s) reflected from the surface. Each detector outputs a corresponding color sensor reading indicative of the detected intensity of the reflected wavelength(s), such as red, green, blue, and/or visible spectrum wavelengths. Color sensor 208 may also detect reflected light in the IR and/or UV wavelength ranges. In other examples, color sensor 208 may be a camera-based reader that uses a camera and image processing techniques to capture and analyze an RGB image of the verification area to obtain the color information indicative of the amount of soil remaining on the verification coupon. For purposes of the present description, the term "color sensor readings" will be used to describe the raw color information obtained from reading, scanning, or image analysis of the verification area, and it shall be understood that the disclosure is not limited in this respect.

Computing device 200 receives color sensor readings associated with the verification coupon 100 from the color sensor 208. Clean verification module 206 includes computer readable instructions that, when executed on the one or more processors 202, cause the one or more processors 202 to generate color data from the color sensor readings. Clean verification module 206 further includes computer readable instructions that, when executed on the one or more processors 202, cause the one or more processors 202 to analyze the color data and determine the efficacy of a cleaning process based on the analysis of the color data. Clean verification module 206 may further include computer readable instructions that, when executed on the one or more processors 202, cause the one or more processors 202 to analyze the color data and identify potential failures of one or more cleaning process parameters that may have led to an unsatisfactory cleaning result. Clean verification module 206 may further include computer readable instructions that, when executed on the one or more processors 202, cause the one or more processors 202 to analyze the potential failures of one or more cleaning process parameters that may have led to an unsatisfactory cleaning result and to suggest corrective action(s) that may be taken to address the one or more potential failures.

Clean verification module 206 may further include computer readable instructions that, when executed on the one or more processors 202, cause the one or more processors 202 to communicate with a remote or cloud-based computing device to send and/or receive information associated with a cleaning process verification procedure. In some examples, where the computing device 200 is a remote or cloud-based computer, clean verification module 206 may further include computer readable instructions that, when executed on the one or more processors 202, cause the one or more processors 202 to automatically communicate with a cleaning machine controller (such as dish machine controller 170) to automatically adjust one or more cleaning process parameters of the cleaning machine based on the results of the analysis.

Clean verification module 206 may further include computer readable instructions that, when executed by the one or more processors 202, cause the one or more processors 202 to generate one or more notifications for display on user interface 204 of computing device 200, or on a user interface of another computing device, such as user interface 222 of user computing device 225, regarding the results of the cleaning process verification procedure. For example, FIG. 4B shows computing device 225 (in this example, a smart phone or tablet computer) having a touch screen display 222. Notifications 216 and 218 are displayed on the touch screen 222. Notification 216 indicates that a cleaning process carried out on Aug. 7, 2018, using a verification coupon having Serial No. A10456-52, failed the corresponding cleaning process verification procedure. In other words, analysis of the color data associated with the verification area on verification coupon having Serial No. A10456-52 indicated that the test indicator was not satisfactorily cleaned. Notification 216 may include the word "FAIL" and an (!) indication or other attention-getting icon, for example, to help draw a user's attention to the fact that this particular cleaning process failed, and that one or more problems with the cleaning process may need to be addressed. Notification 218 indicates that a cleaning process carried out on Aug. 7, 2018, using a verification coupon having Serial No. D25432-40, passed the corresponding cleaning process verification procedure. In other words, analysis of the color data associated with the verification area on verification coupon having Serial No. D25432-40 indicated that the test indicator was satisfactorily cleaned. In this example, notification 208 therefore includes the word "PASS" to indicate that the corresponding cleaning process has been verified as satisfactory.

A button 220 displayed on touchscreen 222 and labeled "Scan Next Coupon" or similar may be tapped to enable a user to obtain color data from another verification coupon using the color sensor 208. In some examples, color sensor 208 may be integrated into either one of computing device 200 or computing device 225. In other examples, color sensor 208 may be an external device.

In some examples, notifications 216 and/or 218 on touch screen 222 may be actuated (e.g., selected, touched, or tapped) to cause computing device 225 to display additional information concerning that particular cleaning process verification procedure. For example, tapping notification 216 on touchscreen 222 may cause one or more detailed report(s) concerning the cleaning process carried out on Aug. 7, 2018, using a verification coupon having Serial No. A10456-52, and receiving a FAIL to be displayed on touchscreen 222. The more detailed report(s) may include, for example, information such as the date and time of the cleaning cycle, a unique identification of the cleaning machine, a unique identification of the person running the cleaning process and/or the cleaning verification procedure, the type of articles cleaned during the cleaning process, the types of racks or trays used during the cleaning process, the type of article being cleaned during the cleaning process, the types and amounts of chemical product dispensed during each cycle of the cleaning process, the volume of water dispensed during each cycle of the cleaning process, a "pass" or "fail" indication for the cleaning process, and/or any other information relevant to the cleaning process or the cleaning process verification procedure. The more detailed report(s) may further include information concerning the color data, the analysis of the color data, and/or the results of the analysis of the color data. The report(s) may further include identification of failures in one or more cleaning process parameters that may have resulted in the unsatisfactory results of the cleaning process, and/or suggested corrective action for addressing the failures. Tapping or touching notification 218 on touchscreen 222 may cause processor(s) 202 to generate for display one or more similar detailed report(s) concerning the cleaning process carried out on Aug. 7, 2018, using a verification coupon having Serial No. D25432-40 and receiving a PASS. The more detailed reports may include further interactive regions on the touch screen display that allow a user to drill-down to any level of detail regarding the analysis and/or the results, and/or to adjust one or more settings for the analysis, and/or to perform further analysis of the color data as desired.

Storage media 214 of computing device 200 include data 210 used or generated by computing device 200 during execution of the clean verification module or any other functionality of computing device 200. For example, storage media 214 may include color sensor readings and other information received from color sensor 208, data entered by a user via user interface components 204, and/or color data and any other data used or generated by clean verification module 206 during execution of a cleaning process verification procedure.

Figure 5B:
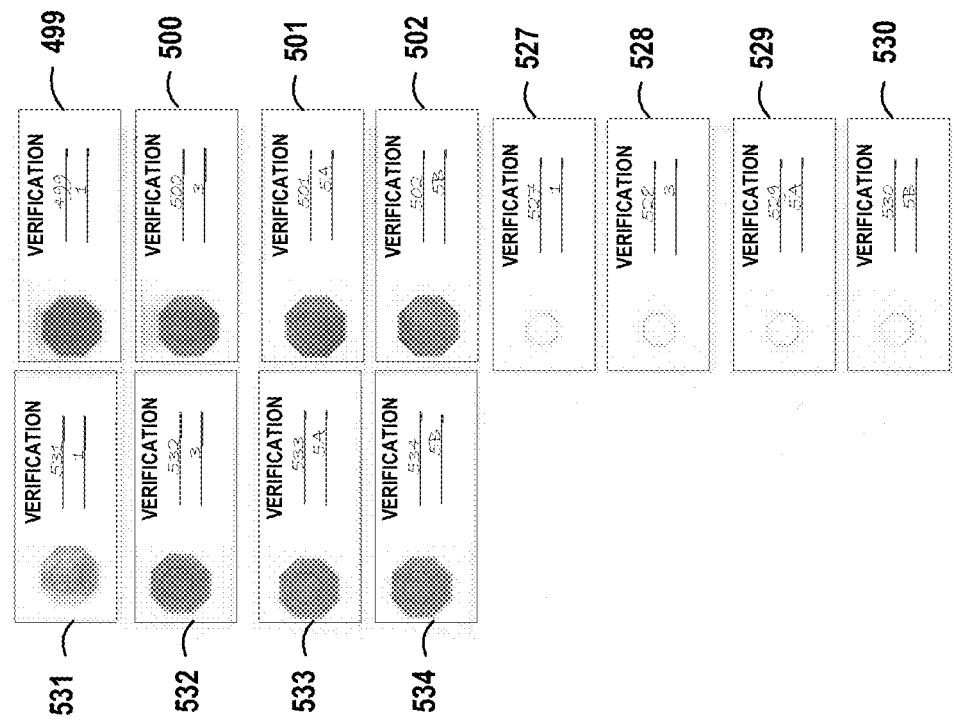
FIGS. 5A and 5B are photographs showing example experimental verification coupons having various levels of "clean" that may be used as part of a training data set to train a computing system to determine optimized cleaning process parameters for an automated cleaning machine.
Figure 5A:
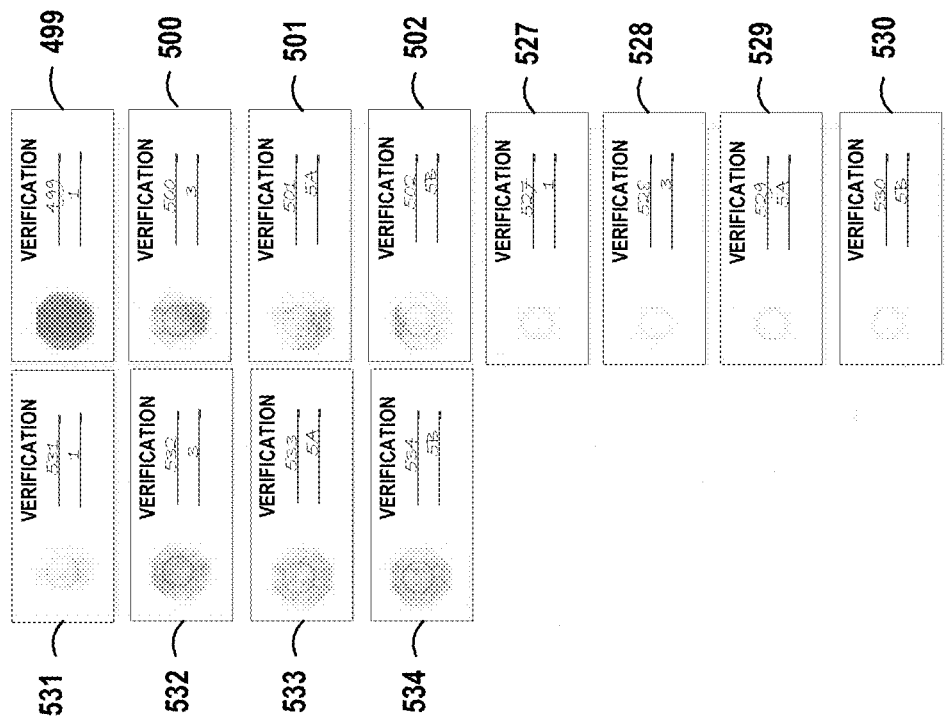

FIG. 5A is a photograph showing example verification coupons 499-502 and 527-534 corresponding to twelve experimental dishmachine cleaning cycles having different cleaning process parameters. In this example, coupons 499-502 and 527-534 are the same type of verification coupon having the same characteristic, red colored, food-based soil. Coupons 499-502 and 527-534 of FIG. 5A show the amount of soil remaining on each coupon after completion of the corresponding experimental cleaning cycle. FIG. 5B shows the same verification coupons 499-502 and 527-534 as in FIG. 5A but with the remaining soil stained with a Coomassie blue dye to visibly show the residual protein.

Table 1 (below) shows the relative % soil removal calculated from RGB color sensor values for the 12 dishmachine cycles corresponding to the coupons of FIG. 5A. The percent soil removal was determined based on RGB color ratio(s) obtained from the coupons as well as RGB color ratio(s) from a "clean" coupon and an unused "soiled" coupon (e.g., a verification coupon that has not been exposed to a cleaning process).

In the example of Table 1, the column labeled "RGB Color Ratio Value" is the calculated red/green (RG) ratio calculated from the color sensor readings associated with the verification coupon. In some examples, for verification coupons including a red colored characteristic food stain, the red/green ratio may be relatively more indicative of percent soil remaining/removed than, for example, the red/blue ratio or the blue/green ratio. However, as described herein, the color data may also include one or more RGB ratios such as a red/green ratio (R/G), a red/blue ratio (RB), a blue/green (B/G) ratio, and/or a C/G color ratio. In addition, or alternatively, the color data may include one or more percent color values. The percent color values may include, for example, a percent red (% R), a percent blue (% B), and/or a percent green (% G). The color data may further include a FIJI gray value, or any other color data indicative of the amount of soil remaining on the verification coupon. In general, the type(s) of color data that are relatively more indicative of percent soil removal may vary depending upon the type of soil on the verification coupon, the color of the soil on the verification coupon, and other factors, and it shall therefore be understood, therefore, that the disclosure is not limited to use of the particular color data shown in Table 1.

For the data in Table 1, the percent soil removal corresponding to a "clean" cleaning prediction was defined as greater than 95.5% soil removal. For some coupons in this example (e.g., coupon 530 in Table 1), the percent soil removal is greater than 100% because the cleaning process also removed some of the small red stop sign under the characteristic soil (not always removed as it is not a part of the soil), so it was more "white" than the clean baseline reading.

TABLE 1

| Coupon | Detergent Concentration (ppm) | RGB Color Ratio Value (RG) | % Soil Removal | Cleaning Prediction |
|---|---|---|---|---|
| 499 | 1582.87 | 1.24 | 65 | Soiled |
| 500 | 1582.87 | 1.15 | 76.25 | Soiled |
| 501 | 1582.87 | 1.09 | 83.75 | Soiled |
| 502 | 1582.87 | 1.02 | 92.5 | Soiled |
| 527 | 2080.27 | 0.962 | 99.75 | Clean |
| 528 | 2080.27 | 0.961 | 99.875 | Clean |
| 529 | 2080.27 | 0.962 | 99.75 | Clean |
| 530 | 2080.27 | 0.958 | 100.25 | Clean |
| 531 | 961.12 | 1.02 | 92.5 | Soiled |
| 532 | 961.12 | 1.16 | 75 | Soiled |
| 533 | 961.12 | 1.13 | 78.75 | Soiled |
| 534 | 961.12 | 1.125 | 79.375 | Soiled |

In this example, the detergent concentration was varied and the percent soil removal was determined based on the RG color data. Similar experiments may be conducted during an optimization phase by varying one or more of the wash time, the rinse time, the detergent type, the water hardness, the sump pH, the wash temperature, the rinse temperature, and any other cleaning cycle parameters. The numeric color data and corresponding percent soil removal may be stored as training data to generate a predictive model for use in determining efficacy of a cleaning process by means of analysis of color data from a verification coupon. The cleaning process parameters that yield consistently "clean" results based on color analysis of verification coupons may be defined as optimized cleaning process parameters. These optimized cleaning process parameters values (or ranges of values) may be stored as the cleaning process parameters for use in automated cleaning machines of the same type on which the empirically determined optimized cleaning process parameters were derived during an optimization phase. In this way, articles subjected to a cleaning process using the optimized cleaning process parameters for the cleaning machine should achieve a "clean" result as long as the optimized cleaning process parameters are met.

Figure 6:
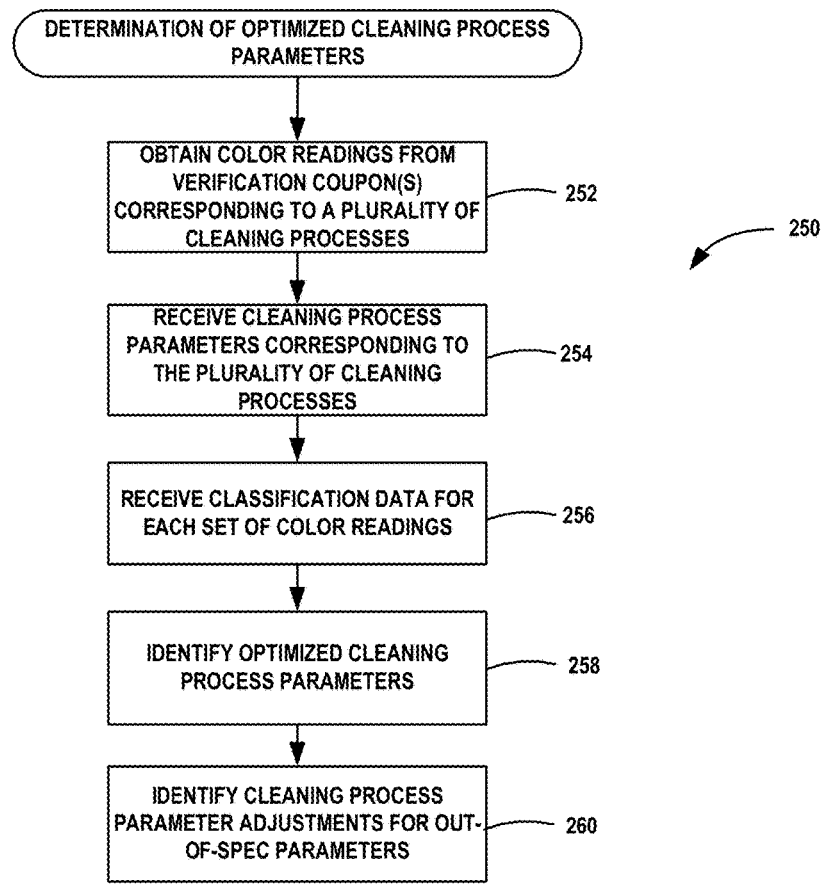
FIG. 6 is a flowchart illustrating an example process by which a computing device may determine optimized cleaning process parameters in accordance with the present disclosure.

FIG. 6 is a flowchart illustrating an example process (250) by which a computing device may determine optimized cleaning process parameters based on color readings from verification coupon(s) corresponding to a plurality of cleaning processes during an optimization phase. The optimization phase may be an experimental or training phase which includes execution of one or more cleaning processes and varying one or more cleaning process parameters. The cleaning process parameters that may be varied may include the wash time, the rinse time, the detergent type, the water hardness, the sump pH, the wash temperature, the rinse temperature, and/or any other cleaning cycle parameters. The color readings, color data, and corresponding clean result (such as percent soil removed or other measure of "clean" or "soiled") may be stored as training data to generate a predictive model for determination of optimized cleaning process parameters for a cleaning machine or type of cleaning machine. The cleaning process parameters that yield consistently "clean" results based on color analysis of verification coupons may be defined as optimized cleaning process parameters. These optimized cleaning process parameters values (or ranges of values) may be stored as the optimized cleaning process parameters for use in automated cleaning machines of the same type on which the empirically determined optimized cleaning process parameters were identified during the optimization phase. In this way, articles subjected to a cleaning process using the optimized cleaning process parameters for the cleaning machine should achieve a "clean" result as long as the optimized cleaning process parameters are met.

The computing device may include a local computing device, such as a mobile computing device, a smart phone, a tablet computer, a laptop computer, a desktop computer, a server computer, a personal digital assistant (PDA), a portable gaming device, a portable media player, an e-book reader, a wearable computing device, a smartwatch, a television platform, or any other type of computing device. The computing device may also include a remotely located computing device, such as one or more server computing device(s) or cloud-based computing system.

In the example of FIG. 6, the computing device receives or obtains color sensor readings from one or more verification coupons corresponding to a plurality of experimentally designed cleaning processes (252). The computing device also receives the cleaning process parameters corresponding to each of the plurality of cleaning processes (254). The cleaning process parameters are varied such that the relationship between each cleaning process parameter and the cleaning process result (e.g., clean, soiled, percent soil removal/remaining, etc.) may be determined by analysis of the color sensor readings from each verification coupon. Classification data corresponding to each color sensor reading is also obtained (256). In other words, each color sensor reading and corresponding color data may be classified during the optimization or training phase as to whether the result corresponds to "clean", "soiled", a percent soil removed or percent soil remaining, or classified as to one or more other measure(s) of the cleaning result.

The computing device identifies optimized cleaning process parameters based on the color readings, the cleaning process parameters, and the classification data corresponding to each cleaning process (258). The optimized cleaning process parameters may include a minimum threshold value for one or more of the cleaning process parameters, a maximum threshold value for one or more of the cleaning process parameters, or a threshold range of values for one or more of the cleaning process parameters.

The computing device may also identify adjustments to one or more cleaning process parameters to compensate for non-optimal or out-of-spec cleaning process parameters based on the color readings, the cleaning process parameters, and the classification data corresponding to each cleaning process (260). In other words, the computing device may identify how certain of the cleaning process parameter(s) may be adjusted in the event that a particular cleaning process parameter is not satisfying the optimized value(s) for that particular cleaning process parameter. For example, the computing device may determine that, in the event the detergent concentration sensed is not within an optimized detergent concentration range, the duration of the wash cycle should be extended a predetermined period of time to compensate for the failure of the detergent concentration to satisfy its optimized value and therefore to help ensure a satisfactory cleaning result. In this way, an automated cleaning machine may be programmed with the cleaning process parameter adjustments to self-adjust during execution of a real-world cleaning process and help ensure a satisfactory cleaning result is achieved even though the detergent concentration (or other cleaning process parameter(s)) failed to satisfy its optimized value.

Figure 7:
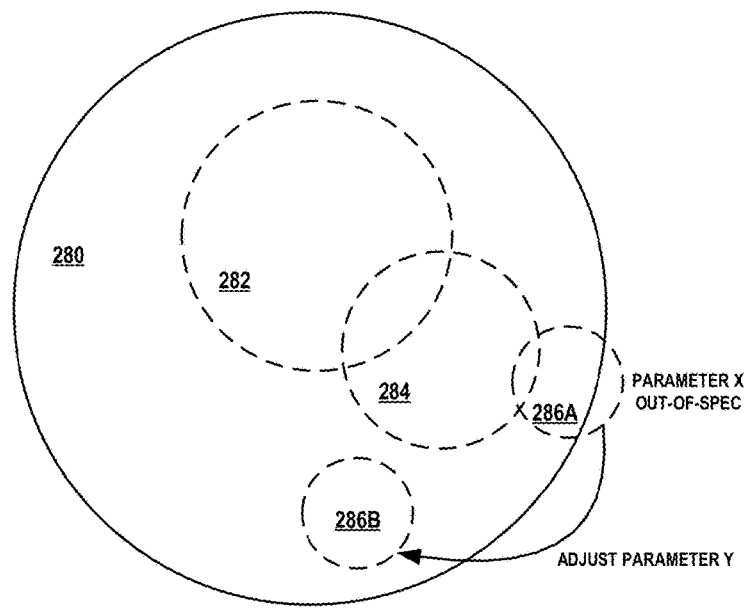
FIG. 7 is a diagram illustrating adjustment of one or more cleaning process parameters to compensate for failure of another cleaning process parameter to satisfy its optimized cleaning process parameter value(s) in accordance with the present disclosure.

FIG. 7 is a diagram illustrating adjustment of one or more cleaning process parameters to compensate for failure of another cleaning process parameter to satisfy its optimized cleaning process parameter value(s). A domain 280 represents the entire set of optimized cleaning process parameters by which a satisfactory or "clean" result may be achieved by a cleaning process in an automated cleaning machine. The machine may be programmed to execute a cleaning process with these optimized cleaning process parameters within domain 280. Sub-domain 282 represents the particular set of cleaning process parameters sensed during execution of a first cleaning process by the cleaning machine. Sub-domain 284 represents the particular set of cleaning process parameters sensed during execution of a second cleaning process by the cleaning machine, and sub-domain 286 represents the particular set of cleaning process parameters sensed during execution of a third cleaning process by the cleaning machine. For sub-domain 282 and 284, the sensed cleaning process parameters are within domain 280 and therefore the cleaning process parameters each satisfy the thresholds for the optimized cleaning process parameter, and therefore a "clean" result should be achieved. For sub-domain 286A, which is associated with the third cleaning process, at least one cleaning process parameter, designated cleaning process parameter x, has failed to satisfy its associated optimized cleaning process parameter. The third cleaning process represented by sub-domain 286A is thus outside of optimized domain 280. This means that a "clean" result will not be achieved with the cleaning process parameters sensed during the third cleaning process represented by sub-domain 286A. By adjusting a different cleaning process parameter, designated cleaning process parameter y, as determined during the training or optimization phase, the third cleaning process may be brought back into domain 280 as represented by sub-domain 286B. In this way, a cleaning machine may be programmed to self-adjust during execution of a cleaning process to help ensure a satisfactory cleaning result is achieved even when certain of the cleaning process parameters fail to satisfy their optimized threshold values.

Figure 8:
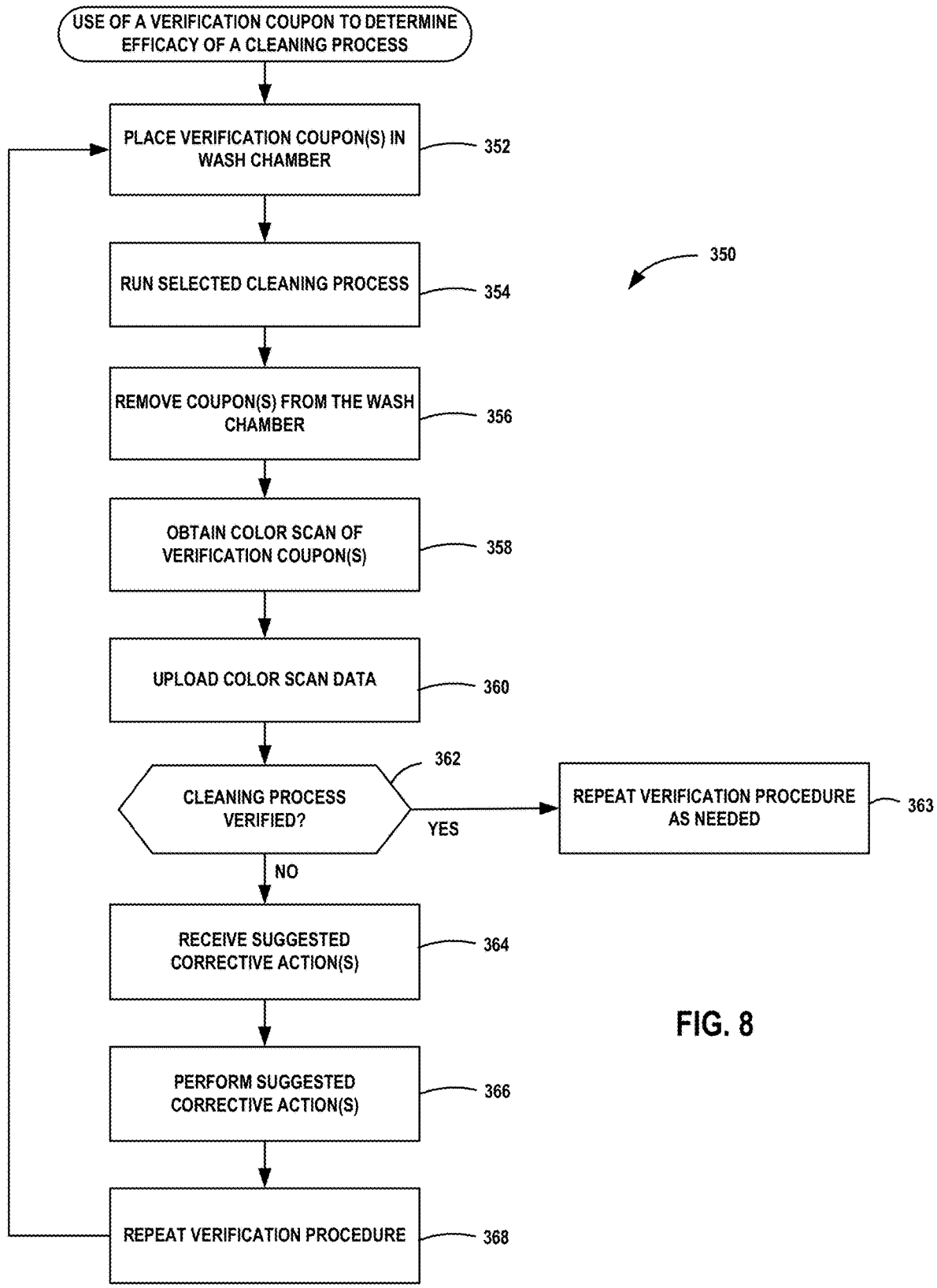
FIG. 8 is a flowchart illustrating an example process by which a cleaning process may be verified in accordance with the present disclosure.

FIG. 8 is a flowchart illustrating an example verification procedure (350) which may be used to verify efficacy of a cleaning process in an automated cleaning machine by analysis of color data associated with a verification coupon in accordance with the present disclosure.

To begin the cleaning process verification procedure (350), a user places one or more cleaning process verification coupon(s), such as coupon(s) 100 as shown in FIG. 1, in the wash chamber of an automated cleaning machine (352). In some examples, the verification procedure is conducted when the cleaning machine is otherwise empty; in other words, the verification procedure is conducted when there are no articles to be cleaned in the wash chamber of the cleaning machine. In other examples, the verification procedure is conducted when articles to be cleaned are present in the wash chamber during the verification procedure. In some examples, a cleaning process verification protocol established by the entity may specify whether articles to be cleaned should or should not be present during the cleaning process verification procedure.

The user may include one or more of an employee of an establishment in which the cleaning machine is located, a service technician, a sales representative, or any other person tasked with the responsibility of running a cleaning process verification procedure. The cleaning process verification procedure (350) may be run periodically to confirm that articles subject to cleaning processes within the automated cleaning machine are adequately cleaned. In general, if the verification coupons do not indicate a "clean" result, the machine may not be hitting one or more optimized machine settings (otherwise referred to herein as optimized cleaning process parameters or optimized wash cycle parameters), and corrective action may be required.

The automated cleaning machine may include any type of dishwasher or warewashing machine, including commercial dishwashers, warewashers, sanitizers, high or low temperature machines, conveyor dishwashers, door-type dishwashers, under counter dishwashers, glass washers, pot/pan/utensil washers, etc. The automated cleaning machine may also include any type of medical cleaning equipment, including washer/decontaminators, steam sterilizers, autoclaves, ultrasonic washers, tunnel washers, cart washers, etc. The automated cleaning machine may also include laundry machines or any other type of cleaning machine. It shall therefore be understood that the disclosure is not limited with respect to the type of automated cleaning machine or the articles to be cleaned.

Once the verification coupon(s) are placed in the wash chamber of the cleaning machine (352), the cleaning machine is run through the selected cleaning process (354). When the cleaning process is complete, the user removes the cleaning process verification coupon(s) from the wash chamber of the cleaning machine (356). As a result of the cleaning process, the test indicator(s) on each the cleaning process verification coupon(s) will be removed or changed in some way that is a function of the efficacy of the cleaning process.

To verify the cleaning process (that is, to test or confirm the efficacy of the cleaning process), a color sensor (such as color sensor 208 in FIG. 4A) may be used to scan the verification area (such as verification areas 102 of FIGS. 1 and 2) of the verification coupon, and to obtain color sensor readings associated with the verification area. The color sensor readings are indicative of an amount of test indicator (soil) remaining in the verification area after completion of the cleaning process (358).

For example, the color sensor may include a light source and one or more photodetectors. Each photodetector detects an amount of red, green, blue, and/or visible spectrum wavelengths reflected from the verification area, and outputs corresponding color sensor readings indicative of the detected intensity of the reflected wavelength(s). The color sensor may also detect reflected light in the IR and/or UV wavelength ranges.

The color scan data is uploaded to a computing device (360), and a clean verification application on the computing device (such as clean verification module 206 in computing device 200) analyzes the received color sensor readings associated with the verification area. As part of the analysis, the computing device 200 may generate color data from the color sensor readings, including one or more of a red/green ratio, a blue/green ratio, a red/blue ratio, a percent red, a percent green, a percent blue, a FIJI gray value, or any other color data that may be used to characterize or quantify the amount of color present in the verification area. The results of the analysis, and any associated cleaning score (such as "Pass", "Fail", or other determined level of clean or soiled)

may be displayed on the user computing device (such as shown in FIG. 4B), and these results may be viewed by the user (362). If the analysis of the color data indicates that the test indicator was satisfactorily cleaned (YES branch of 362), the clean verification application will verify the cleaning process, and generate, for example, a "Pass" indication for display. When the cleaning process is verified as satisfactory, no corrective action is necessary, and the verification process may be repeated as necessary or as specified by a clean verification protocol (363).

If the analysis of the color data indicates that the test indicator was not satisfactorily cleaned (NO branch of 362), the cleaning verification application may generate, for example, a "Fail" indication for display. The indication may further include one or more suggested corrective action(s) that may be taken to address any potential problems identified with respect to one or more cleaning process variables (366). The suggested corrective action(s) may include one or more possible reason(s) for the failure (e.g., mechanical failure, chemistry failure, user error, or combination of these) and/or corrective action(s) that may address the cause of the failure to help ensure that the cleaning machine is working properly or ensure adequate cleaning in subsequent cycles. For example, failures during a cleaning cycle can be a result of failures of one or more cleaning process parameters, including improper chemical cleaning agent(s), improper chemical cleaning agent concentration(s), insufficient water pressure, poor water quality (hardness or turbidity), incorrect wash or rinse water temperatures, incorrect wash or rinse cycle durations, operator error, mechanical failures, and/or other factors. The verification procedure may be repeated as necessary or desired (368).

Although the example process (350) shown in FIG. 8 is described as at least a partially manual process in the sense that a user places the verification coupon(s) into the cleaning chamber of a washing machine, removes the verification coupon(s) from the cleaning machine, and scans the verification coupon to obtain a color sensor reading associated with an amount of soil remaining on the coupon, it shall be understood that some or all of such process may be automated, and that the disclosure is not limited in this respect. For example, an automatic verification coupon feeder may advance verification coupon(s) into the wash chamber, and a color sensor may automatically capture color sensor readings associated with the verification area of the verification coupon upon completion of the cleaning process. For example, the dishmachine controller 170 of FIG. 3 may include or interface to a color sensor that automatically captures color data associated with the verification area of a verification coupon upon completion of the cleaning process.

Figure 9:
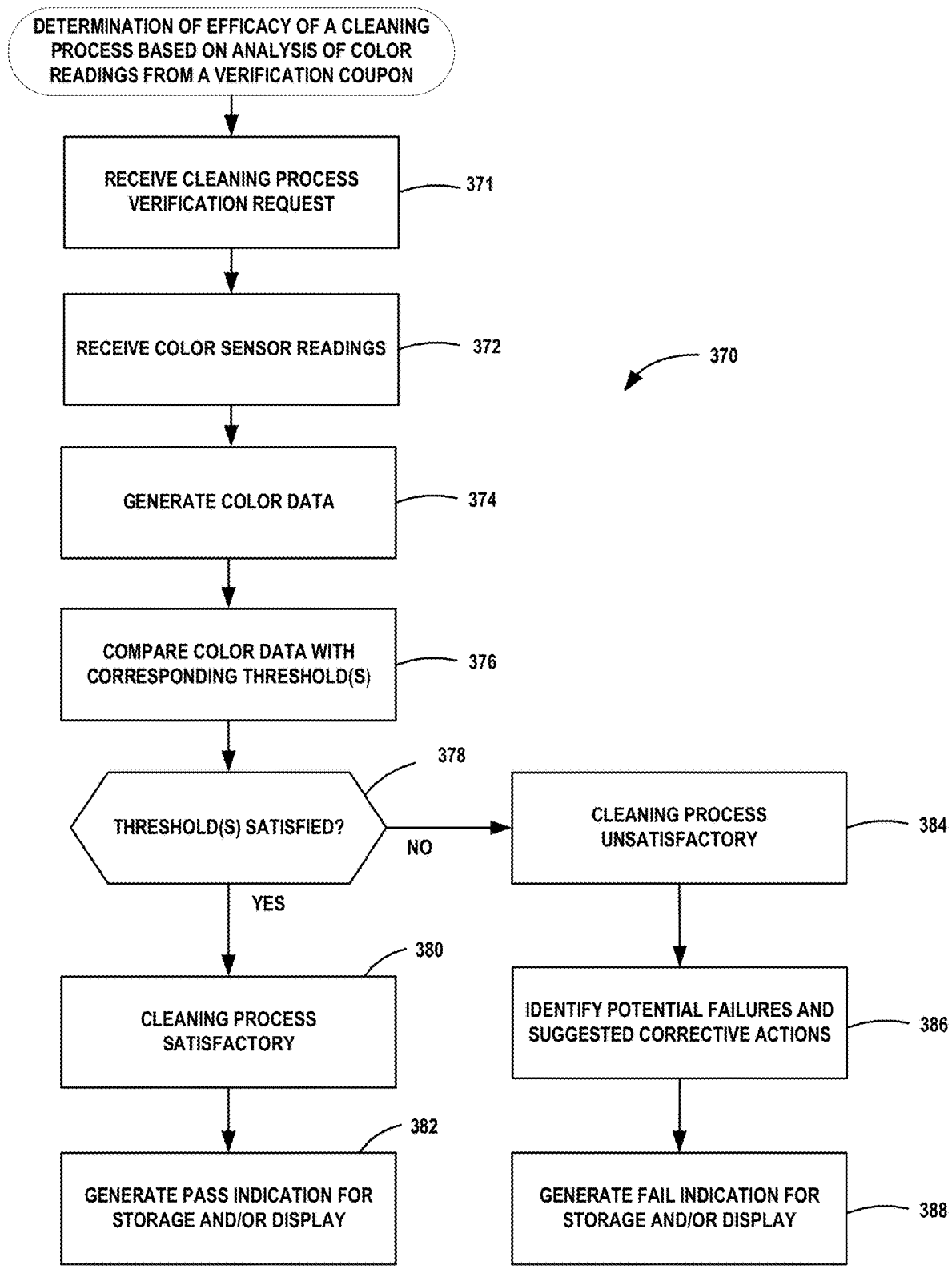
FIG. 9 is a flowchart illustrating an example process by which a computing device may verify efficacy of a cleaning process by analyzing color sensor readings associated with a verification coupon in accordance with the present disclosure.

FIG. 9 is a flowchart illustrating an example process (370) by which a computing device (such as computing device 200 as shown in FIGS. 4A and/or 4B) may verify efficacy of a cleaning process by analyzing color sensor readings associated with a verification coupon in accordance with the present disclosure. The computing device may include one or more remotely located computing device(s), such as a server computer or group of computers, that provides a cloud-based computing service that monitors/or and manages cleaning processes carried out by one or more automated cleaning machines. For example, the computing device(s) may analyze color sensor readings associated with one or more verification coupons, determine optimized cleaning process parameters, monitor real-world cleaning processes for compliance with optimized parameters, determine adjusted cleaning process parameters, suggest corrective action when cleaning process parameters are out-of-spec or when analysis of color sensor readings of a verification coupon indicate unsatisfactory cleaning result, generate one or more reports concerning data gathered during or about the cleaning processes, and/or perform any other cleaning process monitoring or management tasks. The computing device may also include a local computing device, such as a mobile computing device, a smart phone, a tablet computer, a laptop computer, a desktop computer, a server computer, a personal digital assistant (PDA), a portable gaming device, a portable media player, an e-book reader, a wearable computing device, a smartwatch, a television platform, or any other type of computing device.

In the example of FIG. 9, the computing device receives a cleaning process verification request (371). As part of the verification process, the computing device receives color sensor readings associated with a verification area on the cleaning process verification coupon corresponding to an amount of test indicator (soil) remaining after completion of the cleaning process (372). The computing device analyzes the color sensor readings to calculate color data associated with the verification coupon (374). The color data may include one or more RGB ratios, one or more percent color values, a FIJI gray value, one or more of an intensity, an opacity, or any other type of color data. Each component or type (e.g., RGB ratio(s), FIJI gray value, percent color value(s), intensity, opacity, etc.) of the color data is compared with one or more corresponding threshold(s) indicative of a satisfactory result of the cleaning process (376). The threshold(s) may include one or more of a minimum threshold value, a maximum threshold value, a range of threshold values, etc. The type of threshold may be different for each component of the color data.

For example, the color data may include one or more of a red-green (RG) color ratio, an red-blue (RB) color ratio, a green-blue (GB) color ratio, and/or a CG color ratio. The color data may also include a percent color value (% R, % B, and/or % G) and/or a FIJI gray value. Each color ratio may be compared to one or more corresponding threshold(s). Thus, in this example, the RG color ratio is compared to one or more corresponding RG threshold(s), the RB color ratio is compared to one or more corresponding RB threshold(s), the GB color ratio is compared to an one or more corresponding GB threshold(s), and the CG color ratio is compared to one or more corresponding CG color ratio(s). Similarly, the FIJI gray value may be compared to one or more corresponding FIJI gray threshold(s). Likewise, if one or more percent color values are used in the analysis, a % R is compared to a corresponding % R threshold(s), a % G is compared to a corresponding % G threshold(s), and a % B is compared to a corresponding % B threshold(s). Other types of color data calculations or combinations may also be compared to one or more corresponding color data thresholds, depending upon what type of color data is statistically significant in evaluating efficacy of a cleaning process for a particular type and color of test indicator.

If the analysis of the color data satisfies the corresponding threshold(s) (YES branch of 378) this means that the test indicator was adequately removed by the cleaning process, and the computing device may verify that the cleaning process "Passes" the verification procedure (380). The computing device may generate a "Pass" indication for display on the user interface of the computing device (382), such as shown in FIG. 4B, for example.

If the analysis of the color data does not satisfy the associated threshold(s) (NO branch of 378), the test indicator was not adequately removed from the substrate by the cleaning process, and the cleaning process thus "Fails" the verification procedure (384) The computing device may generate a "Fail" indication for display on the user interface of the computing device (388), such as shown in FIG. 4B, for example.

In addition, in the event of an unsatisfactory cleaning result, the computing device may further analyze the color data with respect to the cleaning process parameters to identify potential reason(s) why the results of the cleaning process were unsatisfactory (386). For example, failure of certain of the color data to satisfy one or more parameter-specific thresholds may indicate potential problems with one or more of the cleaning process parameters. The fail indication (388) may further include an identification of the potential failures in the cleaning process and suggested corrective actions that may be taken to address the potential failures.

Figure 10:
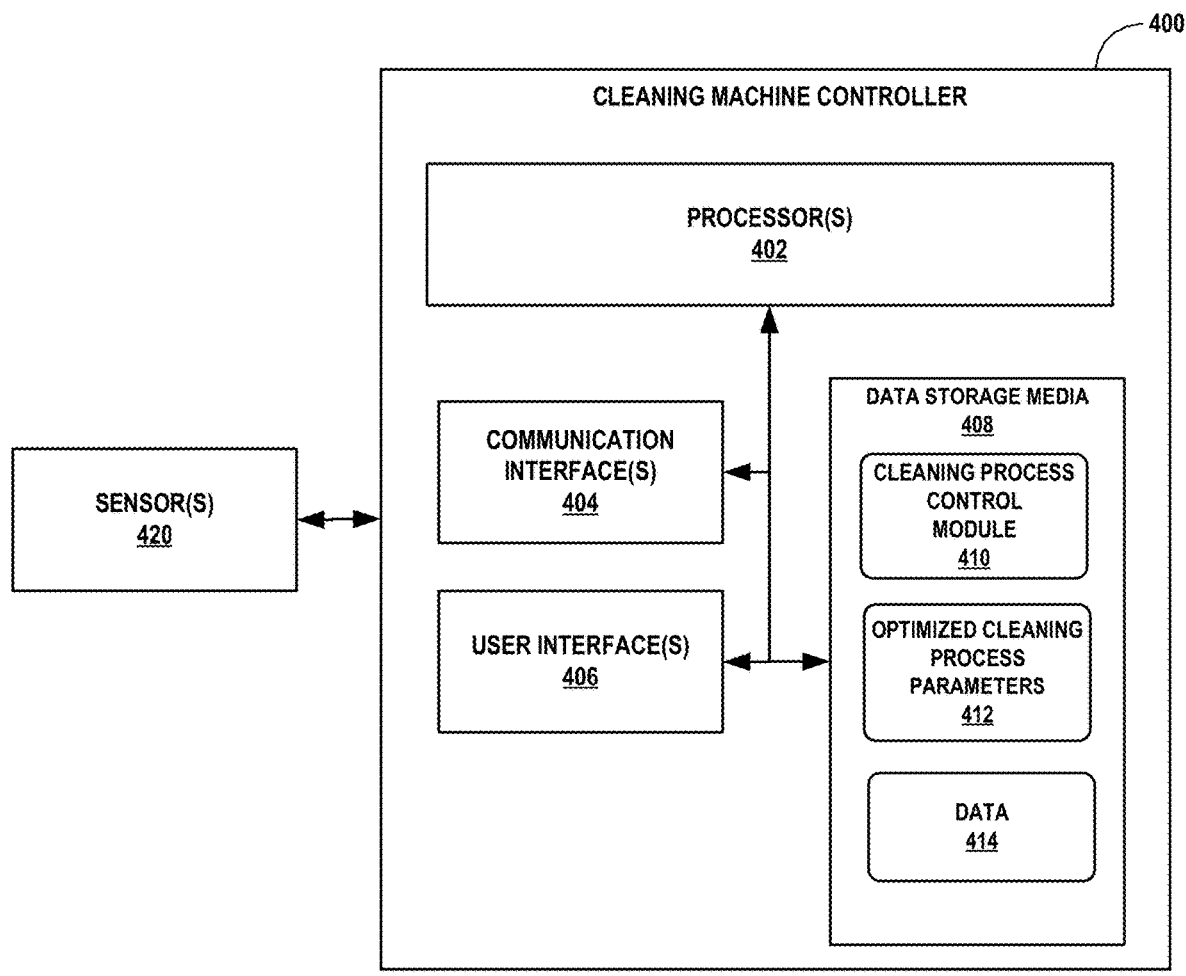
FIG. 10 is a block diagram of an example cleaning machine controller programmed to automatically adjust one or more cleaning process parameters during execution of a cleaning process.

FIG. 10 is a block diagram of an example cleaning machine controller 400 programmed to automatically adjust one or more cleaning process parameters during execution of a cleaning process to compensate for failure of a sensed cleaning process parameter to satisfy its associated optimized parameter value. Controller 400 includes one or more processors 402, one or more user interface components 406, one or more communication interfaces 404, and data storage media 408. User interface components 406 may include one or more audio or visual indicators and/or touch-based interface components, including, for example, a touch screen display, buttons, keypad, or other mechanism that allows a user to interact with the cleaning machine. Communication interfaces 404 allow controller 400 to communicate with other remote or local computing devices via wired and/or wireless connections. The wired and/or wireless communication may include communication over one or more networks, such as any type of Local or Wide Area Networks, including Wi-Fi networks, Bluetooth communication, Near Field communication, and/or the internet. Data storage media 408 includes a cleaning process control module 410, optimized cleaning process parameter storage 412, and data storage 414. Cleaning process control module 410 includes computer readable instructions that, when executed by the one or more processors 402, cause the one or more processors 402 to control operation of a cleaning process, analyze sensor data received during a cleaning process to determine whether any of the cleaning process parameters are out-of-spec with respect to each other, and to automatically adjust one or more cleaning process parameters in the event that any of the cleaning process parameters are determined to be out-of-spec (e.g., not satisfying the optimized parameter values).

Cleaning machine controller 400 may receive input from one or more sensors 420 that sense actual values of cleaning process parameters during a real-world cleaning process. Sensor(s) 420 may include, for example, one or more temperature sensor(s), a sump turbidity sensor, a conductivity sensor, a pH sensor, a flow sensor, a pressure sensor, or any other sensor capable of sensing the actual values of one or more cleaning process parameters during or associated with a cleaning process. In accordance with instructions contained in cleaning process control module 410, the sensed cleaning process parameters may be compared to the optimized cleaning process parameters 412. If controller 400 senses a difference between the optimized cleaning process parameters and any sensed (actual) cleaning process parameters, cleaning process control module 410, when executed by the one or more processors 402, may cause the controller 400 to automatically adjust one or more cleaning process parameters to compensate for any non-optimized cleaning process parameters that are sensed during the cleaning process. In this way, the automated cleaning machine may self-adjust to compensate for any non-optimized cleaning process parameters to help avoid a potentially unsatisfactory cleaning result.

Figure 11:
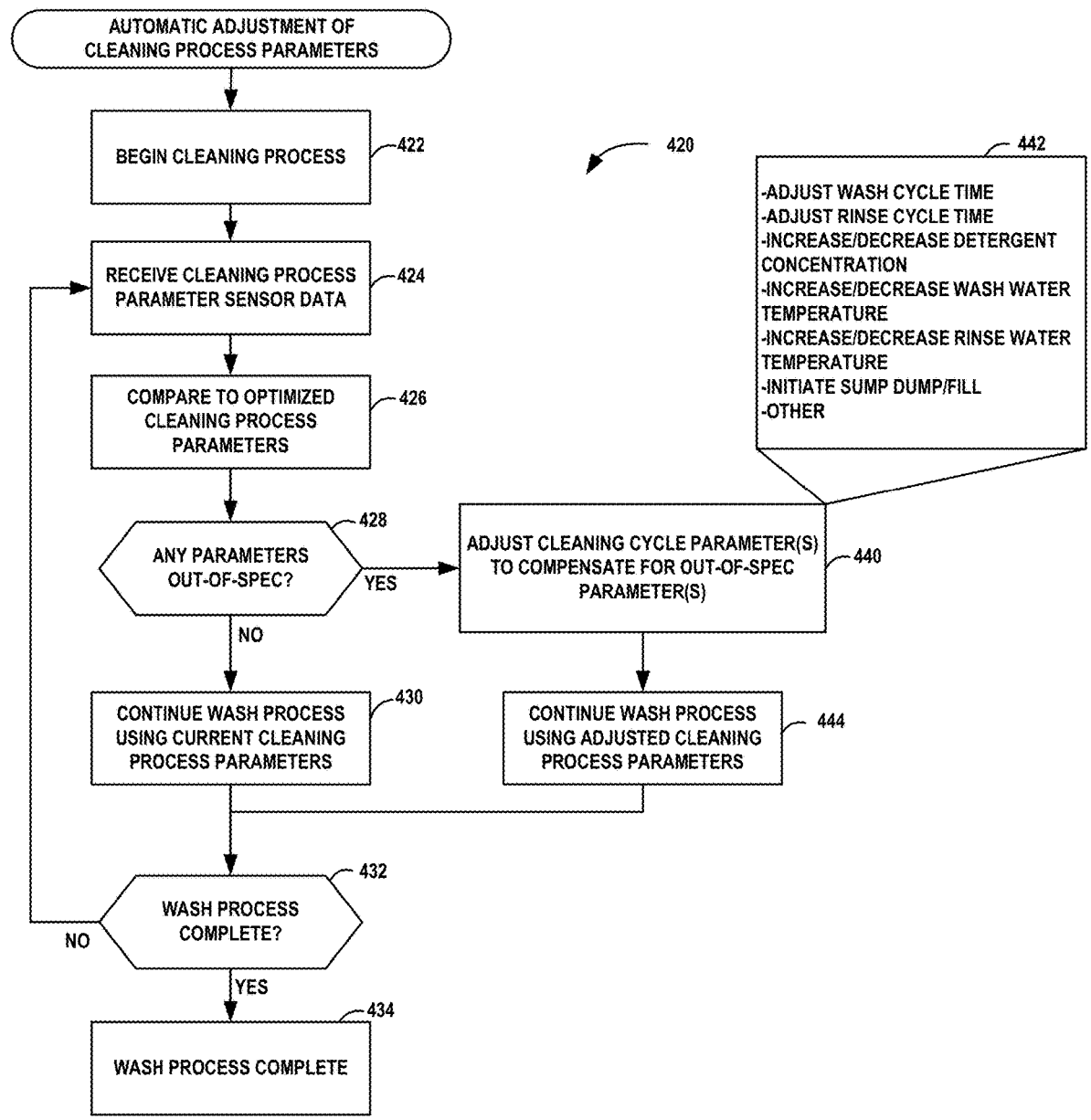
FIG. 11 is a flowchart illustrating an example process by which a computing device may automatically adjust one or more cleaning process parameters in accordance with the present disclosure.

FIG. 11 is a flowchart illustrating an example process (420) by which a computing device (such as cleaning machine controller 400 as shown in FIG. 10) may automatically adjust one or more cleaning process parameters to compensate for failure of one or more cleaning process parameters to satisfy their respective target parameter value(s). The computing device initiates the cleaning process (422) and receives cleaning process parameter data from one or more sensor(s) associated with the cleaning machine. At least some of the sensed cleaning process parameter data has corresponding optimized cleaning process parameter values which, so long as the cleaning machine stays within the predefined optimized ranges for those cleaning process parameters, a satisfactory cleaning result should be achieved. To help ensure a satisfactory cleaning result, computing device compares the sensed cleaning process parameter values to the corresponding stored optimized parameter values (426). If any of the sensed cleaning process parameters are out-of-spec (e.g., they do not fall within the target or threshold range or satisfy the target or threshold values for the corresponding cleaning process parameter) (YES branch of 428), the computing device may adjust one or more different cleaning process parameter(s) to compensate for the cleaning process parameter that failed to satisfy its optimized parameter value(s) (440).

For example, depending on which cleaning process parameter failed to satisfy its optimized parameter value, and/or how the cleaning process parameter failed to satisfy its optimized parameter value (e.g., sensed value too high, sensed value too low, etc.) the computing device may do any one or more of the following: extend or increase the wash cycle duration; decrease the wash cycle duration; extend or increase the rinse cycle duration; decrease the rinse cycle duration; increase the detergent concentration; decrease the detergent concentration; increase a rinse aid concentration; decrease a rinse aid concentration; increase the wash (sump) water temperature; decrease the wash (sump) water temperature; increase the rinse water temperature; decrease the rinse water temperature; increase the incoming water temperature; decrease the incoming water temperature; initiate a sump water dump/fill cycle; initiate a de-liming cycle; and/or perform any other cleaning process parameter adjustment (442). The cleaning process then continues using the adjusted cleaning process parameters (444) to help ensure that a satisfactory cleaning result is achieved even though certain of the cleaning process parameters did not satisfy their respective optimized parameter values.

If the sensed cleaning process parameters fall within their respective target or threshold range or satisfy the respective target or threshold values (NO branch of 428), the computing device continues the cleaning process using the current cleaning process parameters (430). The process continues (432) until the cleaning process is complete (434).

Figure 12:
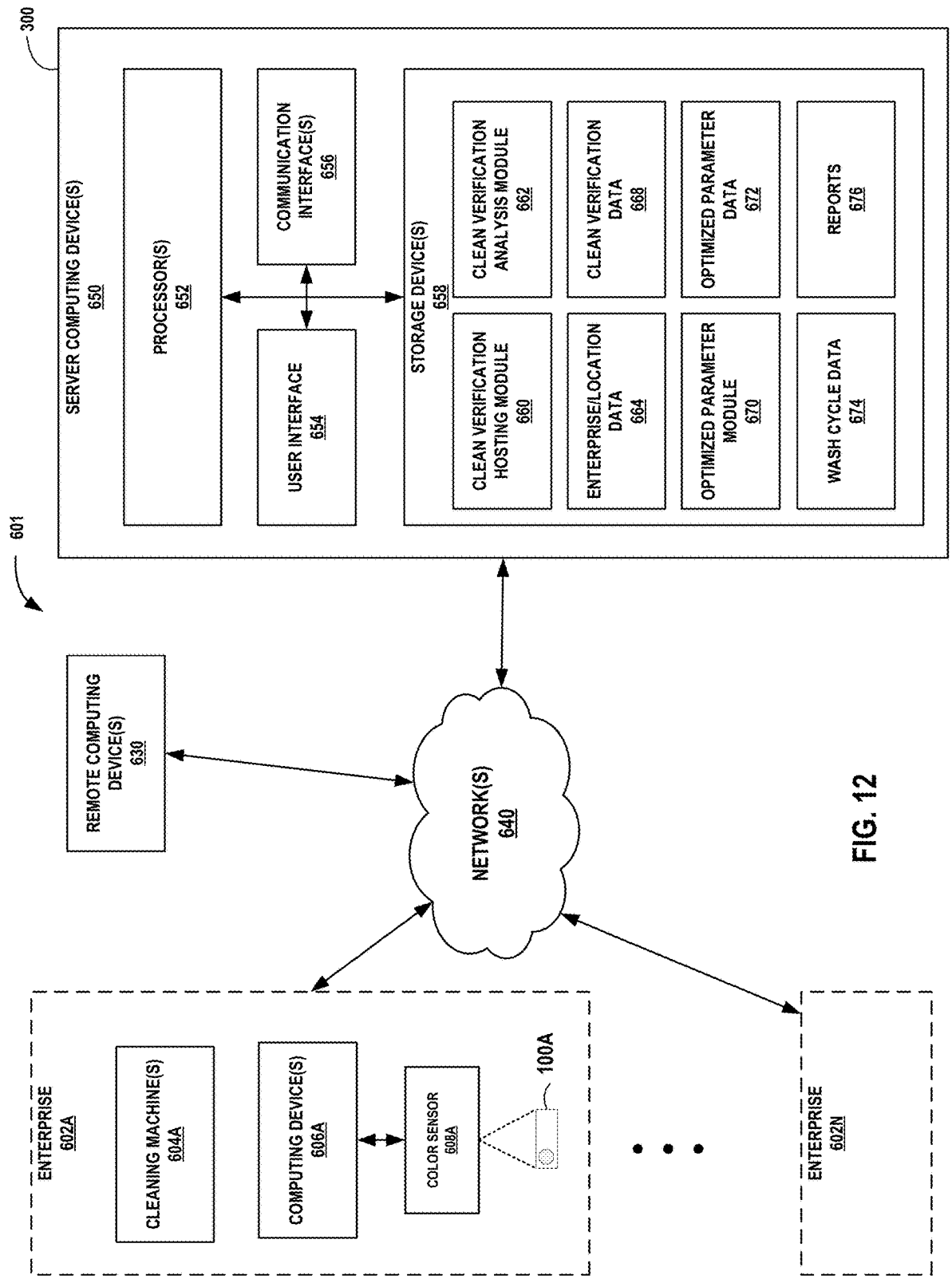
FIG. 12 is a block diagram of a computing system environment that uses analysis of color readings associated with one or more verification coupons in accordance with the present disclosure.

FIG. 12 is a block diagram of a computing system environment 601 that uses analysis of color readings associated with one or more verification coupons in accordance with the present disclosure. One or more enterprises 602A-602N each include one or more cleaning machines 604A-604N and one or more computing devices 606A-606N, respectively. The computing devices 606A-606N may receive color sensor readings acquired from color scans of verification coupons 100A-100N by color sensors 608A-608N, respectively. The color readings may be transmitted over network(s) 640 to server computing device 650 for analysis.

Server computing device(s) 650 may remotely receive and analyze color sensor readings associated with one or more cleaning processes collected by local computing device(s) 606A-606N. In this sense, server computing device(s) 650 may provide a so-called cloud-based service for verification of cleaning processes taking place at one or more locations or enterprises 602A-602N associated with each of computing device(s) 606A-606N, respectively.

Server computing device(s) 650, local computing devices 606A-606N, and remote computing device(s) 630 communicate using one or more network(s) 640. Network(s) 640 may include, for example, one or more of a dial-up connection, a local area network (LAN), a wide area network (WAN), the internet, a wireless or Wi-Fi network, a cell phone network, satellite communication network, Bluetooth, Zigbee, near field communication (NFC) and/or any other means of short- or long-range electronic communication. The communication within network(s) 640 may be wired or wireless or any combination thereof. Remote computing device(s) 630 may include, for example, one or more of a server computing device, a desktop computing device, a laptop computing device, a tablet computing device, a mobile computing device (such as a smart phone) a personal digital assistant, a pager, or any other type of computing device. Color sensors 608A-608N may be used to capture color sensor readings associated with one or more verification coupon(s) 100A-100N and transmit the color sensor readings to an associated one of the plurality of local computing devices 606A-606N. In some examples, the local computing devices 606A-606N may be associated with a single user, enterprise, business entity or location. In other examples, some of the local computing devices 606A-606N are associated with one enterprise, business entity or location, and other of the local computing devices 606A-606N are associated with a separate, unrelated, enterprise, business entity or location. In a chain restaurant environment, for example, some of local computing devices 606A-606N may be associated with a different location of the chain restaurant, while each of local computing devices 606A-606N are associated with the same parent corporation or business enterprise. At the same time, other of local computing devices 606A-606N may be associated with entirely separate and unrelated locations or business entities, such as one or more different restaurants, hotels, healthcare facilities or other locations/business entities in which cleaning processes are verified using verification coupons as described herein.

Server computing device(s) 650 includes one or more processor(s) 652 and one or more data storage media 658. Server computing device(s) 650 may further include one or more user interface components 654 and one or more communication interface components 656. The communication interface components 656 allow server computing device(s) 650 to communicate with one or more of computing device(s) 606A-606N and remote/local computing device(s) 630 via network(s) 640.

Storage media 658 include a clean verification hosting module 660, a clean verification analysis module 662, enterprise/location data 664, clean verification data 668, optimized parameter determination module 670, optimized parameter data 672, wash cycle data 674, and storage for one or more reports 676.

Clean verification hosting module 660 includes computer readable instructions that, when executed on the one or more processors 652, cause processors 652 to host cleaning process verification services for one or more of computing devices 606A-606N. For example, clean verification hosting module 660 may include instructions that enable server computing device 650 to carry out one or more cleaning process verification procedures (e.g., by analyzing color readings obtained from a color scan of a verification coupon that was exposed to the cleaning process), store the results, and communicate the results to the appropriate user computing device(s) 606A-606N, or to remote computing device(s) 630.

Clean verification analysis module 662 includes computer readable instructions that, when executed on the one or more processors 652, cause the processor to receive and analyze the color sensor readings received from computing devices 606A-606N. Clean verification hosting module 660 may further include computer readable instructions that, when executed by the one or more processors 652, cause the one or more processors 652 to generate one or more notifications for display on, for example, a user interface of the appropriate local computing device 606A-606N, regarding the results of the cleaning process verification procedure. For example, the notifications 216 and 218 on touch screen display 222 in FIG. 4B may be generated remotely by server computing device(s) 650 hosting a cloud-based cleaning process verification service rather than locally by user computing device 200.

Enterprise/location data 664 may include data concerning each enterprise and/or location for which server computing device(s) 650 provides clean process verification services. For example, enterprise/location data 664 may include corporate data pertaining to an enterprise or location, location identification information, location type (e.g., restaurant, healthcare facility, etc.) types and identifiers of cleaning machines at each location, cleaning machine rack identifiers associated with each location, employee lists and identification information, data associating one or more computing devices (such as one or more of computing device 606A-606N) with each location or enterprise, corporate and/or location cleaning process targets and tolerances, and other data related to the enterprise, the location, and/or the cleaning processes at each location.

Clean verification data 668 may include color sensor readings received from computing devices 606A-606N and any associated data, such as data entered by a user at the time of the scan, date and time stamps associated with the color sensor readings, etc. Clean verification data 668 may further include data generated by clean verification hosting module 660 or clean verification analysis module 662 during the course of performing cleaning process verification procedures. Wash cycle data 674 may include data obtained or generated for a plurality of wash cycles by cleaning machines 604A-604N present at each of the monitored locations or enterprises 602A-602N. The wash cycle data for each wash cycle may include, for example, a location identifier, a rack identifier, a rack type, a cleaning machine identifier, a date/time stamp, cycle times and lengths, water temperature settings, cleaning machine settings, chemical clean product dispenser settings, times and amounts of chemical cleaning products dispensed, and any other data relevant to a wash cycle. The wash cycle data 674 may further include any sensed cleaning process parameter data including wash and/or rinse cycle start and/or stop times, wash and/or rinse water temperatures, sump temperature, pH, turbidity, conductivity, information related to detergent concentration or rinse aid concentration, or any other information sensed during a cleaning process.

Clean verification hosting module 660 may also include reporting functionality by which server computing device(s) 650 may generate one or more reports concerning cleaning process verification data 668, enterprise/location data 664, and/or wash cycle data 674 for communication to and/or display by one of computing device(s) 606A-606N and/or remote computing device(s) 630. For example, actuation of notification 216 on touchscreen 222 of FIG. 4B may cause a more detailed report concerning the cleaning process carried out on Aug. 7, 2018, using a verification coupon having Serial No. A10456-52, and receiving a FAIL to be generated by server computing device(s) 650 for display on touchscreen 222.

The following is an example detailed report concerning the cleaning process corresponding to verification coupon Serial No. A10456-52, including example cleaning process verification data and associated example wash cycle data.

| Cleaning Cycle Overview | |
|---|---|
| Date/Time | Aug. 7, 2018 02:35:14 |
| Location | Store #302, St. Paul, MN |
| Verification Coupon | Serial No. A10456-52 |
| Clean Verification Score | FAIL |
| Coupon Type | Food Soil 3 |
| Machine Type | Single Rack/High Temperature |
| Rack Type | Dishware |
| Cycle Type | Dishware |
| Employee ID | 555-5555 |

In this example, the water temperature for both the wash cycle and the sanitizing rinse cycle were too low (the wash water temperature for the cleaning cycle was 128° F. and the target water temperature was 155° F. minimum, and the sanitizing rinse water temperature for the cleaning cycle was 145° F. and the target sanitizing rinse water temperature was 180° F. minimum). The reason for the failure of the cleaning cycle to pass the verification procedure may therefore be because the wash cycle and sanitizing rinse water temperatures were too low. The last column of the detailed report includes possible reasons/causes for the failure and/or ways in which to address the failure.

As another example, one or more remote computing device(s) 630 may request reports including data corresponding to one or more specific cleaning processes, or data concerning cleaning processes at one or more specific location(s), cleaning machine(s), date(s), time(s), employee, cleaning score(s), etc. The data may be used to identify trends, areas for improvement, or otherwise assist the person(s) responsible for ensuring the efficacy of cleaning process to identify and address problems in the cleaning processes.

The report(s) may include information for one or more cleaning processes/cycles, and the data for each cleaning process may include information such as the date and time of the cleaning process, a unique identification of the cleaning machine, a unique identification of the person running the cleaning process and/or the cleaning verification procedure, the type of articles cleaned during the cleaning process, the types of racks or trays used during the cleaning

| Cleaning Cycle Details | | | | |
|---|---|---|---|---|
| Parameter | Cycle Data | Specification/Target | Error | Possible Cause |
| Wash Cycle Time | 45 | 45 | | |
| Dwell Time | 8 | 8 | | |
| Rinse Time | 7 | 7 | | |
| Load Time | 5 | 5 | | |
| Total Cycle Time | 65 | 65 | | |
| Wash Water Temp. | 128° F. | 155° F. (minimum) | −27° F. (too low) | faulty temperature sensor<br>faulty heating element<br>water supply temp, too low<br>clogged inlet screen<br>supply hose blocked or kinked<br>rack overloaded |
| Water Consumption | 0.47 gal/rack | 0.47 gal/rack | | |
| Sanitize/Rinse Water Temp | 145° F. | 180° F. (minimum) | −35° F. (too low) | faulty temperature sensor<br>faulty heating element<br>water supply temp, too low<br>clogged inlet screen<br>supply hose blocked or kinked<br>rack overloaded |
| Wash Product | Dishmachine Detergent - All Purpose | Dishmachine Detergent - All Purpose | | |
| Wash Product Dilution | 0.1% | 0.1% | | |
| Rinse Product | Rinse Additive - All Purpose | Rinse Additive - All Purpose | | |
| Rinse Product Dilution | 0.0020% | 0.0020% | | |
| Sanitizer Product | Sanitizer | Sanitizer | | |
| Sanitizer Product Dilution | 0.018% | 0.018% | | | process, the type of article being cleaned during the cleaning process, the types and amounts of chemical product dispensed during each cycle of the cleaning process, the volume of water dispensed during each cycle of the cleaning process, a "pass" or "fail" indication for the cleaning process, an image of the cleaning process verification coupon, or other information relevant to the cleaning process or the cleaning process verification procedure. The report(s) may further include information concerning the how much of the test indicator was removed and/or how much of the test indicator remained. The report(s) may further include information concerning the determined color data corresponding to the verification procedure. The report(s) may further include information on possible reason(s) why the cleaning process failed (e.g., whether a hardware-related failure, chemistry-related failure, or possible user error), and/or suggested correction(s) for addressing the failure. The report(s) may also include information concerning the location; the business entity/enterprise; corporate clean verification targets and tolerances; cleaning scores by location, region, machine type, date/time, employee, and/or cleaning chemical types; energy costs; chemical product costs; and/or any other cleaning process data collected or generated by the system or requested by a user.

Clean verification hosting module 660 and clean verification analysis module 662 include computer readable instructions that, when executed by processor(s) 652, cause processor(s) 652 to receive color data associated with the verification coupon(s) 100A-100N. Clean verification hosting module 660 includes computer readable instructions that, when executed on the one or more processors 652, cause processor(s) 652 to provide cleaning process verification services and, in doing so, to carry out a plurality of cleaning process verification procedures. In some examples, clean verification hosting module 660 includes computer readable instructions configured to be executed on the one or more processors 652 to execute a process similar to the example process (250) as shown in FIG. 6, to execute a process similar to the example process (370) as shown in FIG. 9, or to execute a process similar to the example process (420) as shown in FIG. 11.

For example, server computing device 650 may execute hosting module 660 to manage communication between server computing device(s) 650 and the one or more user computing devices 606A-606N and to execute cleaning process verification procedures between the user computing devices 606A-606N and server computing device 300. For example, server computing device 650 may receive a request for a cleaning process verification procedure and associated color data from one or more of the computing device(s) 606A-606N (371). The color data from each computing device 606A-606N may include color sensor readings associated with the verification area of a verification coupon. Server computing device(s) 650 may analyze the color sensor readings using, for example, clean verification analysis module 662. Analysis module 662 may generate color data based on the received color sensor readings (374). Analysis module 662 may further analyze the color data by, for example, comparing the color data to one or more threshold(s) (376, 378), and determine or verify the efficacy of the cleaning process based on the analysis of the color data.

If the analysis indicates that the color data satisfies the one or more thresholds (378), the efficacy of the cleaning process may be verified satisfactory (380). The server computing device may generate and store and/or transmit a pass indication for display by the associated one of the user computing devices 606A-606N. Alternatively, if the analysis indicates that the color data does not satisfy the one or more thresholds, the results of the cleaning process are unsatisfactory (384). The server computing device may further identify potential failures and suggested corrective actions that may be taken to address the potential failures (386). The server computing device 650 may generate and transmit a fail indication for display by the associated one of the user computing devices 606A-606N (388).

Although the examples presented herein are described with respect to automated cleaning machines for medical or food preparation/processing applications, it shall be understood that the cleaning process verification techniques described herein may be applied to a variety of other applications. Such applications may include, for example, laundry applications, agricultural applications, hospitality applications, and/or any other application in which cleaning, disinfecting, or sanitizing of articles may be useful.

In one or more examples, the functions described herein may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used may refer to any of the foregoing structure or any other structure suitable for implementation of the techniques described. In addition, in some examples, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially.

In some examples, a computer-readable storage medium may include a non-transitory medium. The term "non-transitory" may indicate that the storage medium is not embodied in a carrier wave or a propagated signal. In certain examples, a non-transitory storage medium may store data that can, over time, change (e.g., in RAM or cache).

EXAMPLES

Example 1

A system that determines efficacy of a cleaning process based on color data from a verification coupon that was exposed to the cleaning process, wherein the color data includes at least one of a red-green ratio, a blue-green ratio, a red-blue ratio, or a percent color value.

Example 2

A method for determining efficacy of a cleaning process based on color data from a verification coupon that was exposed to the cleaning process, wherein the color data includes at least one of a red-green ratio, a blue-green ratio, a red-blue ratio, or a percent color value.

Example 3

A method of training a computer system to determine efficacy of a cleaning process based on color data from a plurality of verification coupons that were exposed to a plurality of experimental cleaning processes, wherein the color data includes at least one of a red-green ratio, a blue-green ratio, a red-blue ratio, or a percent color value.

Example 4

An automated cleaning machine that receives sensed values for one or more cleaning process parameters during execution of a cleaning process, determines whether one or more of the sensed values do not satisfy their respective optimized cleaning process parameter values, and adjusts a cleaning machine setting associated with a different one of the cleaning process parameters to ensure a satisfactory cleaning result during execution of a subsequent cleaning process.

Example 5

An automated cleaning machine comprising: at least one processor; at least one sensor that senses information concerning one or more cleaning process parameters during execution of a cleaning process in a wash chamber of the cleaning machine; and a storage device comprising instructions executable by the at least one processor to: receive the sensed information concerning the one or more cleaning process parameters during execution of the cleaning process; determine, based on the sensed information, whether one or more of the cleaning process parameters sensed during execution of the cleaning process does not satisfy a corresponding optimized cleaning process parameter value; and adjust a cleaning machine setting associated with a different one of the cleaning process parameters.

Example 6

The system of Example 5, wherein the one or more cleaning process parameters sensed during execution of the cleaning process include a wash cycle duration, a rinse cycle duration, a detergent concentration, a wash water temperature and a rinse water temperature.

Example 7

The system of Example 5, wherein the one or more cleaning process parameters sensed during execution of the cleaning process include a rinse aid concentration or an incoming water temperature.

Example 8

The system of Example 5, wherein the one or more cleaning process parameters includes a wash water temperature, and wherein the adjusted cleaning machine setting includes a wash cycle duration.

Example 9

The system of Example 5, wherein the one or more cleaning process parameters includes a detergent concentration, and wherein the adjusted cleaning machine setting includes a wash cycle duration.

Example 10

The system of Example 5, wherein the one or more cleaning process parameters includes a wash water temperature, and wherein the adjusted cleaning machine setting includes a detergent concentration.

Example 11

The system of Example 5, wherein the storage device further comprises instructions executable by the at least one processor to initiate a sump water dump/fill cycle.

Example 12

The system of Example 5, wherein the storage device further comprises instructions executable by the at least one processor to initiate a de-liming cycle.

Example 13

The automated cleaning machine of Example 5, wherein the storage device further comprises instructions executable by the at least one processor to: generate a notification indicating that one or more of the cleaning process parameter values sensed during execution of the cleaning process did not satisfy the corresponding optimized cleaning process parameter value.

Example 14

The automated cleaning machine of Example 13, wherein the storage device further comprises instructions executable by the at least one processor to: generate a notification including one or more corrective actions that may be taken to address a failure of the one or more cleaning process parameters to satisfy the corresponding optimized cleaning process parameter value.

Example 15

The automated cleaning machine of Example 5, wherein the storage device further comprises instructions executable by the at least one processor to: apply the adjusted cleaning process parameters during execution of the cleaning process.

Example 16

The automated cleaning machine of Example 5, wherein the storage device further comprises instructions executable by the at least one process to: apply the adjusted cleaning process parameters during execution of a subsequent cleaning process.

Example 17

A non-volatile computer-readable storage medium storing instructions that, when executed, cause one or more processors to: receive sensed information concerning one or more cleaning process parameters during execution of a cleaning process within a wash chamber of a cleaning machine; determine, based on the sensed information, that one or more of the cleaning process parameters sensed during execution of the cleaning process does not satisfy a corresponding optimized cleaning process parameter value; and adjust a cleaning machine setting associated with a different one of the cleaning process parameters.

Example 18

A system comprising: an automated cleaning machine comprising: at least one processor; at least one sensor that senses information concerning one or more cleaning process parameters during execution of a cleaning process in a wash chamber of the cleaning machine; and a storage device comprising instructions executable by the at least one processor to: receive the sensed information concerning the one or more cleaning process parameters during execution of the cleaning process; determine, based on the sensed information, that one or more of the cleaning process parameters sensed during execution of the cleaning process does not satisfy a corresponding optimized cleaning process parameter value; and adjust a cleaning machine setting associated with a different one of the cleaning process parameters.

Example 19

The system of Example 18, further comprising: a computing device comprising: at least one processor; a storage device comprising instructions executable by the at least one processor of the computing device to: obtain color data from a verification coupon that was exposed to the cleaning process, wherein the color data includes at least one of a red-green ratio, a blue-green ratio, a red-blue ratio, or a percent color value; and determine an efficacy of the cleaning process based on the color data.

Example 20

The system of Example 19 wherein the characteristic soil includes a food-based soil.

Example 21

The system of Example 19 wherein the characteristic soil includes an organic soil.

Various examples have been described. These and other examples are within the scope of the following claims.

The invention claimed is:
1. An automated cleaning machine comprising:
a wash chamber;
at least one processor;
at least one sensor; and
one or more storage devices comprising instructions executable by the at least one processor that, when executed, cause the at least one processor to:
 execute a first plurality of cleaning processes in the wash chamber;
 obtain color sensor readings of a plurality of verification coupons exposed to the first plurality of cleaning processes, wherein one or more values of cleaning process parameters are adjusted between each cleaning process of the first plurality of cleaning processes, and the cleaning process parameters include at least a first cleaning process parameter and a second cleaning process parameter different from the first cleaning process parameter;
 generate color data from the color sensor readings for the plurality of verification coupons;
 determine, based on the color data, one or more optimized values of the cleaning process parameters for the automated cleaning machine, wherein determining the one or more optimized values of the cleaning process parameters comprises determining, based on the color data, that the optimized values of the cleaning process parameters yield clean results for articles subjected to the first plurality of cleaning processes, wherein the optimized values of the cleaning process parameters include an optimized value of the first cleaning process parameter;
 execute a second cleaning process in the wash chamber of the automated cleaning machine, wherein the second cleaning process occurs at a period of time after the first plurality of cleaning processes;

receive, from the at least one sensor during execution of the second cleaning process, sensed information concerning at least the first cleaning process parameters;

determine, based on the sensed information, that a value of the first cleaning process parameter sensed during execution of the second cleaning process does not satisfy the optimized value of the first cleaning process parameter;

based on the value of the first cleaning process parameter not satisfying the optimized value of the first cleaning process parameter, adjust a cleaning machine setting associated with the second cleaning process parameter; and apply the adjusted cleaning machine setting associated with the second cleaning process parameter during execution of the second cleaning process to achieve the clean result.

2. The automated cleaning machine of claim 1, wherein the cleaning process parameters include at least one of a wash cycle duration, a rinse cycle duration, a detergent concentration, a wash water temperature and a rinse water temperature.

3. The automated cleaning machine of claim 1, wherein the cleaning process parameters include a rinse aid concentration or an incoming water temperature.

4. The automated cleaning machine of claim 1, wherein the cleaning process parameters includes a wash water temperature, and wherein the adjusted cleaning machine setting includes a wash cycle duration.

5. The automated cleaning machine of claim 1, wherein the cleaning process parameters include a detergent concentration, and wherein the adjusted cleaning machine setting includes a wash cycle duration.

6. The automated cleaning machine of claim 1, wherein the cleaning process parameters include a wash water temperature, and wherein the adjusted cleaning machine setting includes a detergent concentration.

7. The automated cleaning machine of claim 1, wherein the one or more storage devices further comprise instructions executable by the at least one processor to initiate a sump water dump/fill cycle.

8. The automated cleaning machine of claim 1, wherein the one or more storage devices further comprise instructions executable by the at least one processor to initiate a de-liming cycle.

9. The automated cleaning machine of claim 1, wherein the one or more storage devices further comprise instructions executable by the at least one processor to:
generate a notification indicating that the value of the first cleaning process parameter sensed during execution of the second cleaning process did not satisfy the optimized value of the first cleaning process parameter.

10. The automated cleaning machine of claim 9, wherein the one or more storage devices further comprise instructions executable by the at least one processor to:
generate a notification including one or more corrective actions that may be taken to address a failure of the value of the first cleaning process parameter to satisfy the optimized value of the first cleaning process parameter.

11. The automated cleaning machine of claim 1, wherein the one or more storage devices further comprise instructions executable by the at least one processor to:
apply the adjusted cleaning machine setting during execution of a cleaning process subsequent to the second cleaning process.

12. The automated cleaning machine of claim 1, wherein the color data includes at least one of a red-green ratio, a blue-green ratio, a red-blue ratio, or a percent color value.

13. A non-volatile computer-readable storage medium storing instructions that, when executed, cause one or more processors to:
execute one or more of a first plurality of cleaning processes in a wash chamber of an automated cleaning machine;
obtain color sensor readings of a plurality of verification coupons exposed to the first plurality of cleaning processes, wherein one or more values of cleaning process parameters are adjusted between each cleaning process of the first plurality of cleaning processes, and the cleaning process parameters include at least a first cleaning process parameter and a second cleaning process parameter different from the first cleaning process parameter;
generate color data from the color sensor readings for the plurality of verification coupons;
determine, based on the color data, one or more optimized values of the cleaning process parameter values for the automated cleaning machine, wherein determining the one or more optimized values of the cleaning process parameters comprises determining, based on the color data, that the optimized values of the cleaning process parameters yield clean results for articles subjected to the first plurality of cleaning processes, wherein the optimized values of the cleaning process parameters include an optimized value of the first cleaning process parameter;
execute a second cleaning process in the wash chamber of the automated cleaning machine, wherein the second cleaning process occurs at a period of time after the first plurality of cleaning processes;
receive, from at least one sensor of the automated cleaning machine during execution of the second cleaning process, sensed information concerning at least the first cleaning process parameters;
determine, based on the sensed information, that a value of the first cleaning process parameter sensed during execution of the second cleaning process does not satisfy the optimized value of the first cleaning process parameter;
based on the value of the first cleaning process parameter not satisfying the optimized value of the first cleaning process parameter, adjust a cleaning machine setting associated with the second cleaning process parameter; and
apply the adjusted cleaning machine setting associated with the second cleaning process parameter during execution of the second cleaning process to achieve the clean result.

14. A system comprising:
at least one processor;
one or more storage devices comprising instructions executable by the at least one processor that, when executed, cause the at least one processor to:
execute a first plurality of cleaning processes in a wash chamber of an automated cleaning machine;
obtain color sensor readings of a plurality of verification coupons exposed to the first plurality of cleaning processes, wherein one or more values of the cleaning process parameters are adjusted between each cleaning process of the first plurality of cleaning processes, and the cleaning process parameters include at least a first cleaning process parameter and a second cleaning process parameter different from the first cleaning process parameter;

generate color data from the color sensor readings for the plurality of verification coupons;

determine, based on the color data, one or more optimized values of the cleaning process parameters for the automated cleaning machine, wherein determining the one or more optimized values of the cleaning process parameters comprises determining, based on the color data, that the optimized values of the cleaning process parameters yield clean results for articles subjected to the first plurality of cleaning processes, wherein the optimized values of the cleaning process parameters include an optimized value of the first cleaning process parameter;

execute a second cleaning process in the wash chamber of the automated cleaning machine, wherein the second cleaning process occurs at a period of time after the first plurality of cleaning processes;

receive, from at least one sensor of the automated cleaning machine during execution of the second cleaning process, sensed information concerning at least the first cleaning process parameter;

determine, based on the sensed information, that a value of the first cleaning process parameter sensed during execution of the second cleaning process does not satisfy the optimized value of the first cleaning process parameter;

based on the value of the first cleaning process parameter not satisfying the optimized value of the first cleaning process parameter, adjust a cleaning machine setting associated with the second cleaning process parameter; and apply the adjusted cleaning machine setting associated with the second cleaning process parameter during execution of the second cleaning process to achieve the clean result.

15. The system of claim 14, further comprising:
a computing device comprising:
the at least one processor; and
the one or more storage devices comprising instructions executable by the at least one processor of the computing device to:
obtain a second color sensor reading of a second verification coupon that was exposed to the second cleaning process;
generate color data from the second color sensor reading for the second verification coupon, wherein the color data includes at least one of a red-green ratio, a blue-green ratio, a red-blue ratio, or a percent color value; and
determine an efficacy of the second cleaning process based on the color data.

16. The system of claim 15, wherein the second verification coupon comprises a test indicator and one or more soils on the test indicator, and wherein the one or more soils includes a food-based soil.

17. The system of claim 15, wherein the second verification coupon comprises a test indicator and one or more soils on the test indicator, and wherein the one or more soils includes an organic soil.

* * * * *

UNITED STATES PATENT AND TRADEMARK OFFICE
CERTIFICATE OF CORRECTION

| | |
|---|---|
| PATENT NO. | : 12,133,619 B2 |
| APPLICATION NO. | : 17/108894 |
| DATED | : November 5, 2024 |
| INVENTOR(S) | : Rachel Marie McGinness et al. |

It is certified that error appears in the above-identified patent and that said Letters Patent is hereby corrected as shown below:

In the Claims

Column 35, Lines 3-4 Claim 1: Replace "parameters" with -- parameter --.

Column 36, Line 39 Claim 13: Replace "parameters" with -- parameter --.

Column 36, Line 48 Claim 13: Replace "parameters" with -- parameter --.

Column 36, Lines 63-64 Claim 14: Replace "the cleaning" with -- cleaning --.

Signed and Sealed this
Fourth Day of March, 2025

Coke Morgan Stewart
*Acting Director of the United States Patent and Trademark Office*